United States Patent
Northcote et al.

(10) Patent No.: US 12,065,420 B2
(45) Date of Patent: Aug. 20, 2024

(54) USES OF BALAENONE AND METHOD OF EXTRACTION THEREOF

(71) Applicant: HARDIE HEALTH LIMITED, Wellington (NZ)

(72) Inventors: Peter Thomas Northcote, Lower Hutt (NZ); Ameet Jonathan Singh, Lower Hutt (NZ)

(73) Assignee: HARDIE HEALTH LIMITED, Wellington (NZ)

( * ) Notice: Subject to any disclaimer, the term of this patent is extended or adjusted under 35 U.S.C. 154(b) by 756 days.

(21) Appl. No.: 17/270,767

(22) PCT Filed: Aug. 28, 2019

(86) PCT No.: PCT/IB2019/057224
§ 371 (c)(1),
(2) Date: Feb. 23, 2021

(87) PCT Pub. No.: WO2020/044245
PCT Pub. Date: Mar. 5, 2020

(65) Prior Publication Data
US 2021/0332023 A1  Oct. 28, 2021

(30) Foreign Application Priority Data
Aug. 29, 2018 (NZ) ........................ 745822

(51) Int. Cl.
*A61K 36/25* (2006.01)
*A61P 31/04* (2006.01)
*C07D 307/93* (2006.01)
*C07D 307/935* (2006.01)

(52) U.S. Cl.
CPC .......... *C07D 307/935* (2013.01); *A61K 36/25* (2013.01); *C07D 307/93* (2013.01); *A61K 2236/333* (2013.01); *A61K 2236/39* (2013.01); *A61P 31/04* (2018.01)

(58) Field of Classification Search
CPC ................ C07D 307/935; A61K 36/25; A61K 2236/39; A61K 2236/333; A61P 31/04
See application file for complete search history.

(56) References Cited

PUBLICATIONS

J W Peterson. Chapter 7 Bacterial Pathogenesis. Baron S, editor. Medical Microbiology. 4th edition. Galveston (TX): University of Texas Medical Branch at Galveston; 1996. NCBI Bookshelf. A service of the National Library of Medicine, National Institutes of Health. pp. 1-21 (Year: 1996).*
L Radlinski and BP Conlon. Antibiotic efficacy in the complex infection environment. Current Opinion in Microbiology 2018, 42:19-24. (Year: 2018).*
Sizar et al. Gram-Positive Bacteria. [Updated May 30, 2023]. StatPearls Publishing, p. 1-6 (Year: 2023).*
Sri Wahyuni et al., "Antiviral activities of Indonesian medicinal plants in the East Java region against hepatitis C virus," *Virology Journal* 10:259, 2013, 9 pages.
Bradacs et al., "In vitro Cytotoxic, Antiprotozoal and Antimicrobial Activities of Medicinal Plants from Vanuatu," *Phytotherapy Research* 24:800-809, 2010.
Goh et al., "Monoterpenoid Phloroacetophenones From *Euodia latifolia*," *Phytochemistry* 29(5):1704-1706, 1990.
Su et al., "Antiplatelet Aggregation Principles from the Stem and Root Bark of *Melicope triphylla*," *Phytotherapy Research* 12:S74-S76, 1998.
Wang et al., "Efficient synthesis of polycycles bearing prenylated, geranylated, and farnesylated citrans: application to 3'-prenylrubranine and petiolin D regiosomer," *Tetrahedron* 67:9179-9184, 2011.
Wu et al., "Structures and Stereochemistry of Melicophyllone A and Hypocholesterolemic Melicophyllone B, Novel Sesquiterpene Lactones from *Melicope triphylla*," *J. Chem. Soc., Chem. Commun.*:956-957, 1988.

* cited by examiner

*Primary Examiner* — Noble E Jarrell
*Assistant Examiner* — Richard Grant Peckham
(74) *Attorney, Agent, or Firm* — Seed IP Law Group LLP

(57) ABSTRACT

Disclosed herein are compositions containing an isolated bioactive compound of Formula (X):

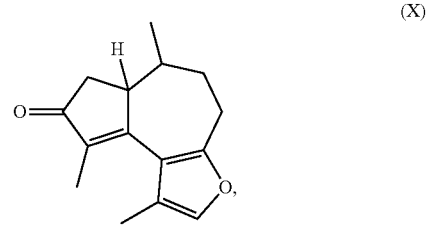

including less than about 2 wt % of halifordin. Also disclosed are methods for obtaining and using compositions containing the isolated bioactive compound.

14 Claims, 14 Drawing Sheets

USES OF BALAENONE AND METHOD OF EXTRACTION THEREOF

1. FIELD OF THE INVENTION

The present invention relates to a novel bioactive compound isolated from the bark of the *Melicope latifolia* tree, compositions comprising the compound and methods of its use.

2. BACKGROUND TO THE INVENTION

*M. latifolia* (previously known as *Euodia latifolia*) belongs to the citrus family Rutaceae. It grows in many countries in Southeast Asia and the Pacific where it is used in traditional medicine. On the island of Loh in Vanuatu, *M. latifolia* is described as an introduced garden plant and is called "nehine". A cold maceration of the leaves is taken internally for the treatment of cough (Bradacs, Maes et al. 2010); (Bradacs, Hellmann et al. 2011).

On peninsula Malaysia, *M. latifolia* is a non-endemic small tree growing in lowland forest and is known in Malay as "Orang Asli". It is considered a threatened species and is used for making resin and soap, as well as in medicine. Pounded leaves are applied externally to bring down fever and to treat cramps (Chooi 1994).

Some extracts of *M. latifolia* materials have been found to have modest bioactivity. An ethanol extract of dried, powdered leaves of *M. latifolia* collected from the Cangar Forest, East Java, Indonesia, was shown to inhibit infection of human liver cells (Huh7.5) cells by the Hepatitis C virus both at the entry and post-entry steps, with an $IC_{50}$ value of 3.5±1.4 µg/mL and a $CC_{50}$ value>100 µg/mL. However, an extract of *M. latifolia* stems was more than 10-fold less effective (Wahyuni, Tumewu et al. 2013).

Extracts of the leaves of *E. latifolia* from Loh in Vanuatu had the following activities (Bradacs, Maes et al. 2010):

The dichloromethane extract had an $IC_{50}$ value of 14.2±0.89 µg/mL against human lung carcinoma cell line A548 in culture.

The dichloromethane and ethyl acetate extracts had $IC_{50}$ values of 8.30±1.43 and 14.94±2.72 µg/mL, respectively, against *Plasmodium falciparum* in red blood cells, but similar activity against human lung fibroblasts (MRC-5SV2) and thus a selectivity index of 1.

The dichloromethane and ethyl acetate extracts had $IC_{50}$ values of 6.55±0.79 and 7.64±0.26 µg/mL, respectively, against *Trypanosoma cruzii* but similar activity against human lung fibroblasts (MRC-5SV2) and thus a selectivity index of 1.

The dichloromethane extract had an $IC_{50}$ value of 8.28±0.62 µg/mL against *Trypanosoma brucei*, but similar activity against human lung fibroblasts (MRC-5SV2) and thus a selectivity index of 1.

While little research has been carried out on extracts of *M. latifolia*, even less is known about the chemistry of its natural products. In what is believed to be the only substantive study of chemical constituents from *M. latifolia*, chromatographic separation of the ethanol extract of dried leaves of *M. latifolia* (known as *Euodia latifolia* at the time) from the Genting Highlands, Pahang, West Malaysia (50 km north of Kuala Lumpur) provided two new isomeric compounds, melifoliones 1a and 1b in 0.006% yield, separated by fractional crystallisation (Goh, Chung et al. 1990).

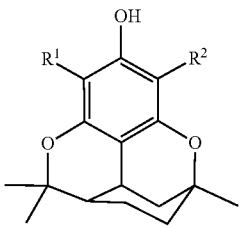

Melifolione (1a) $R^1$ = MeCO, $R^2$ H
Melifolione (1b) $R^1$ = H, $R^2$ MeCO

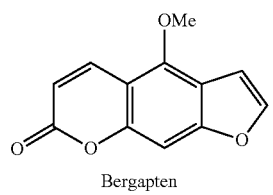

Bergapten (2)

Other compounds isolated were the coumarin derivatives, 5,7,8- and 6,7,8-trimethoxycoumarin, and bergapten (2). Burgapten (2) is the chemical in bergamot oil that causes phototoxicity. It is proposed that levels of such furanocoumarins should be limited in topical formulations. The sterols sitosterol, stigmasterol and campestrol were also found to be present in a 67:17:21 ratio.

The abstract of a Master's thesis (Hashim 2010) reports the isolation of the two alkaloids dictamnine (3) and confusameline (4) from the leaves of *M. latifolia* collected in Sabah, Malaysia.

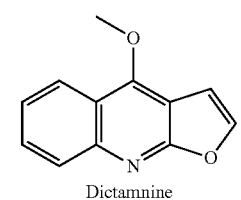

Dictamnine (3)

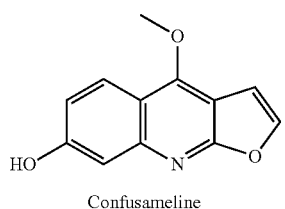

Confusameline (4)

Dictamnine (3) occurs widely in the Rutaceae and is responsible for photo-induced genotoxicity and skin irritation. It has been reported to have anti-platelet aggregation and vascular-relaxing activities (Wu et al., 1994), insecticidal activities, phototoxicity to bacteria and yeast and antibacterial activity against *Mycobacterium smegmatis* and *Bacillus subtilis*. Dictamnine (3) has also been widely used to treat certain skin diseases (Guo, Yu et al. 2008).

Confusameline (4) was found to be the most cytotoxic isolate among a number of furanocoumarins with more potent cytotoxicity ($ED_{50}$ value=0.03 µg/mL) against the P-388 cell line than the reference compound mithramycin ($ED_{50}$ value=0.06 µg/mL) (Chen, Duh et al. 2003).

Two benzopyran compounds, "O-methyloctadrenolone" and alloevodionol (6) were reported as having been isolated from the fruit of *M. latifolia* from Indonesia (Primastuti 2017). However, there appears to be no such compound as "O-methyloctadrenolone", the closest being octadendrolone methyl ether (5), a compound first isolated from New Zealand *M. ternata* (Cambie, Pan et al. 1996).

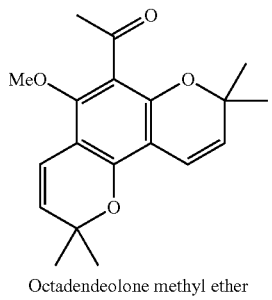

(5)

Octadendeolone methyl ether

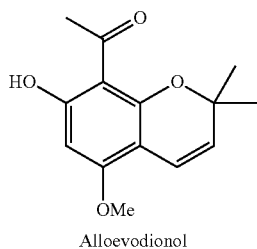

(6)

Alloevodionol

As public health officials recognise the growing problem of antibiotic resistance, researchers are increasing turning to previously unexplored flora and fauna, to find new antibiotic compounds, or at least to provide the public with a useful choice.

The secondary metabolites of *M. latifolia* are relatively unstudied. It is therefore is object of the invention to evaluate this plant for its potential to provide useful bioactive compounds including antibiotic compounds.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

3. SUMMARY OF THE INVENTION

The present invention relates to the isolation and identification of a novel bioactive compound from the bark of the *M. latifolia* tree, named by the inventors as Balaenone.

In one aspect the invention relates to an isolated bioactive compound of Formula (X)

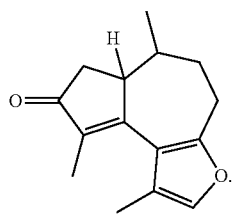

(X)

This compound is herein referred to as "Balaeneone".

In one aspect the invention relates to an isolated bioactive compound of Formula ($X_a$)

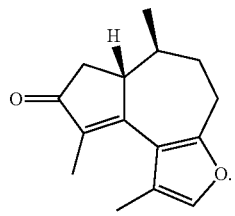

(Xa)

This compound is herein referred to as "1,10-trans-Balaenone" or "trans-Balaenone".

In another aspect the invention relates to an isolated bioactive compound with the structure and relative stereochemistry of Formula ($X_b$).

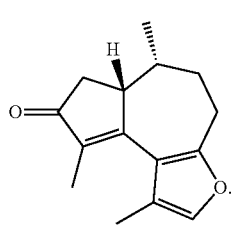

(Xb)

This compound is herein referred to as "1,10-cis-Balaenone" or "cis-Balaenone".

In another aspect the invention relates to a bioactive compound having the NMR spectrum of any one of FIGS. 1-6. In another aspect the invention relates to a bioactive compound having the NMR spectrum of any one of FIGS. 11-16.

In another aspect the invention provides a process of obtaining a purified composition of Balaenone wherein the process comprises the steps of:
 (a) extracting the bark of *M. latifolia* with methanol;
 (b) passing the filtered extract through a PSDVB column which has been pre-equilibrated in methanol;
 (c) combining the eluent with an equal volume of water and passing it through the same PSDVB column;
 (d) washing the column with water;
 (e) eluting the compounds of the adsorbed extract with i) 20% acetone in water (fraction A), ii) 40% acetone in water (fraction B), iii) 60% acetone in water (fraction C), iv) 80% acetone in water (fraction D), and v) acetone (fraction E);
 (f) collecting fractions C and/or D to provide a purified composition of Balaenone; and
 (g) optionally, further purifying fractions C and/or D by silica gel flash chromatography to obtain a more purified composition of Balaenone.

In one embodiment, step (a) is repeated to provide a second methanolic extract.

In one embodiment, step (c) is repeated.

In one embodiment, fractions C and/or D are further purified in step (g) using an ethyl acetate in petroleum ether gradient (0-100%).

In another aspect the invention provides a purified composition of Balaenone obtained by a process comprising the steps of:

(a) extracting the bark of *M. latifolia* with methanol;
(b) passing the filtered extract through a PSDVB column which has been pre-equilibrated in methanol;
(c) combining the eluent with an equal volume of water and passing it through the same PSDVB column;
(d) washing the column with water;
(e) eluting the compounds of the adsorbed extract with i) 20% acetone in water (fraction A), ii) 40% acetone in water (fraction B), iii) 60% acetone in water (fraction C), iv) 80% acetone in water (fraction D), and v) acetone (fraction E);
(f) collecting fractions C and/or D to provide a purified composition of Balaenone; and
(g) optionally, further purifying fractions C and/or D by silica gel flash chromatography to obtain a more purified composition of Balaenone.

In one embodiment, step (a) is repeated to provide a second methanolic extract.

In one embodiment, step (c) is repeated.

In one embodiment, fractions C and/or D are further purified in step (g) using an ethyl acetate in petroleum ether gradient (0-100%).

In another aspect the invention provides a purified composition of Balaenone. In another aspect the invention provides a purified composition of trans-Balaenone. In another aspect the invention provides a purified composition of cis-Balaenone.

In one embodiment, the purified composition comprises at least about 60, 65, 70, 75, 80, 85, 90, 95, 96, 97, 98 or 99 wt % Balaenone. In one embodiment, the purified composition comprises at least about 60, 65, 70, 75, 80, 85, 90, 95, 96, 97, 98 or 99 wt % of trans-Balaenone. In one embodiment, the purified composition comprises at least about 60, 65, 70, 75, 80, 85, 90, 95, 96, 97, 98 or 99 wt % of cis-Balaenone.

In one aspect the invention provides a pharmaceutical composition comprising Balaenone and one or more pharmaceutically acceptable excipients.

In one aspect the invention provides a pharmaceutical composition comprising trans-Balaenone and one or more pharmaceutically acceptable excipients.

In one aspect the invention provides a pharmaceutical composition comprising cis-Balaenone and one or more pharmaceutically acceptable excipients.

In one embodiment the pharmaceutical composition is an anti-bacterial composition.

In another aspect the invention provides a method of treating a bacterial infection in a subject in need thereof, comprising administering to the subject a therapeutically effective amount of Balaenone or a purified composition of Balaenone.

In another aspect the invention provides a method of treating a bacterial infection in a subject in need thereof, comprising administering to the subject a therapeutically effective amount of trans-Balaenone or a purified composition of trans-Balaenone.

In another aspect the invention provides a method of treating a bacterial infection in a subject in need thereof, comprising administering to the subject a therapeutically effective amount of cis-Balaenone or a purified composition of cis-Balaenone.

In one embodiment the infection is a Gram-positive bacterial infection.

The embodiments and preferences set out herein may relate alone or in combination of any two or more to any of the aspects of the invention set out herein.

Although the present invention is broadly as defined above, those persons skilled in the art will appreciate that the invention is not limited thereto and that the invention also includes embodiments of which the following description gives examples.

4. BRIEF DESCRIPTION OF THE DRAWINGS

The invention will now be described with reference to the accompanying Figures in which.

Figure 1:
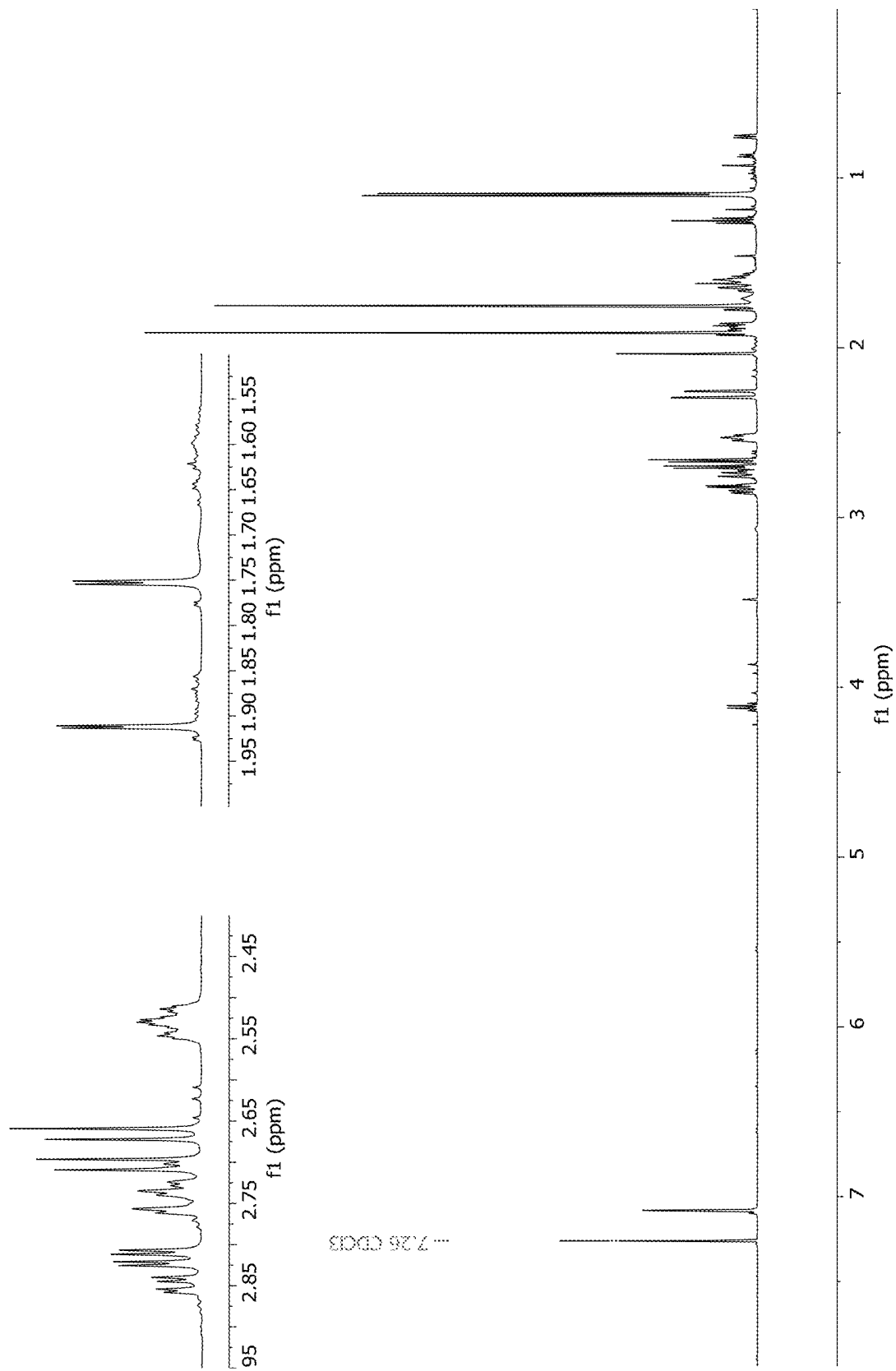
FIG. 1 shows the $^1$H NMR Spectrum of trans-Balaenone in CDCl$_3$.
Figure 2:
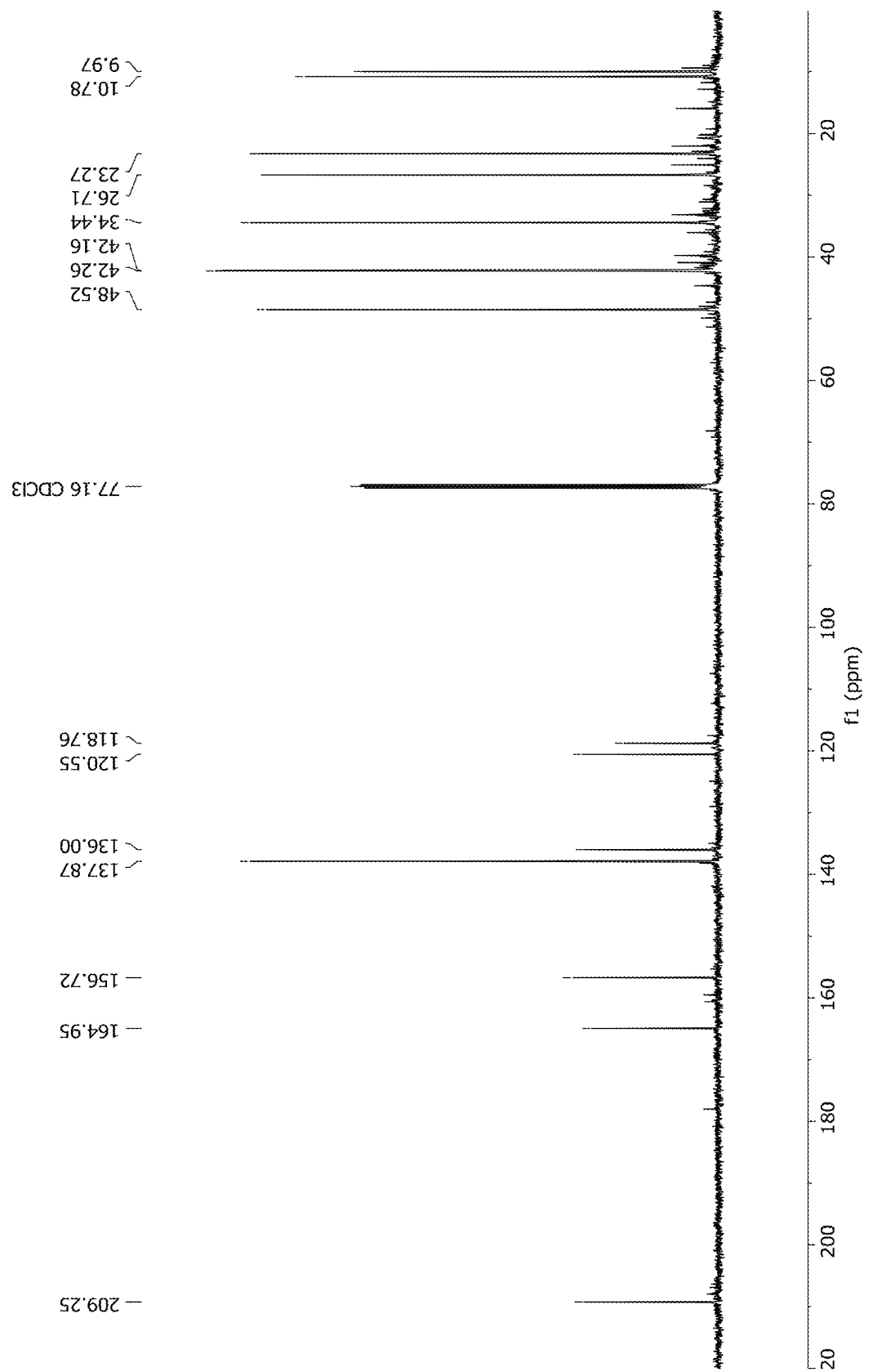
FIG. 2 shows the $^{13}$C NMR (125 MHz) spectrum of trans-Balaenone in CDCl$_3$.
Figure 3:
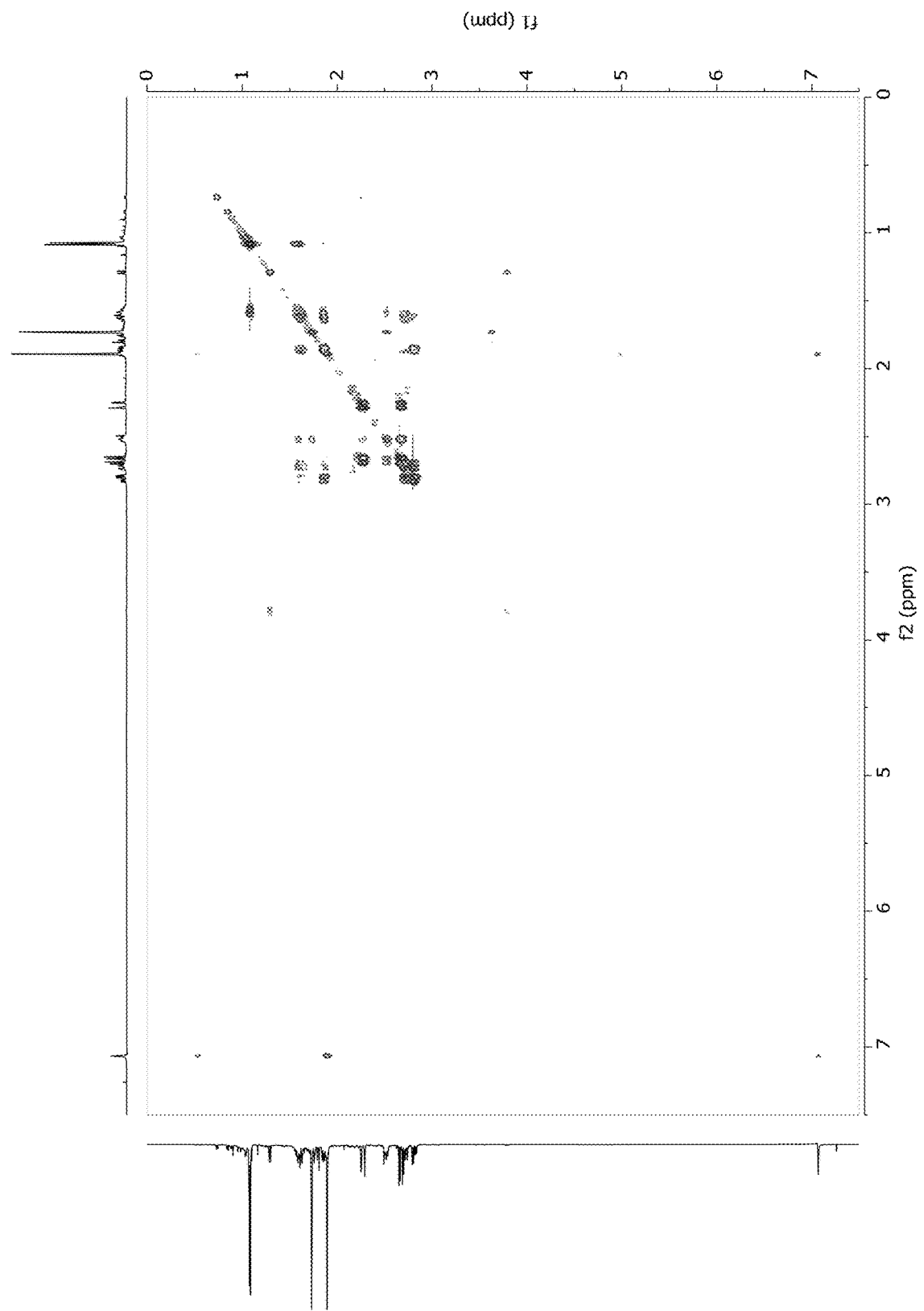
FIG. 3 shows the COSY (500 MHz) spectrum of trans-Balaenone in CDCl$_3$.
Figure 4:
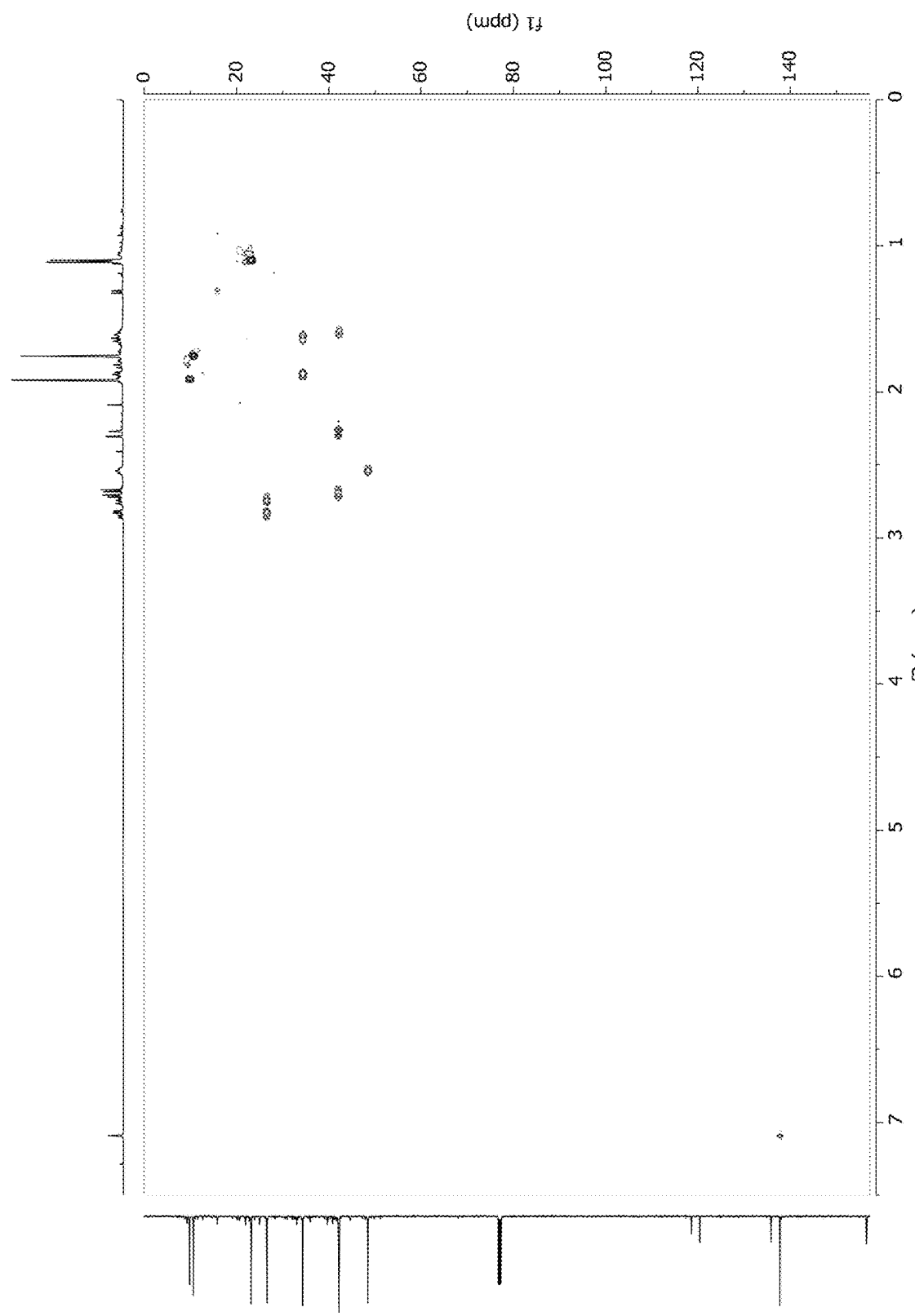
FIG. 4 shows the HSQC (500 MHz) spectrum of trans-Balaenone in CDCl$_3$.
Figure 5:
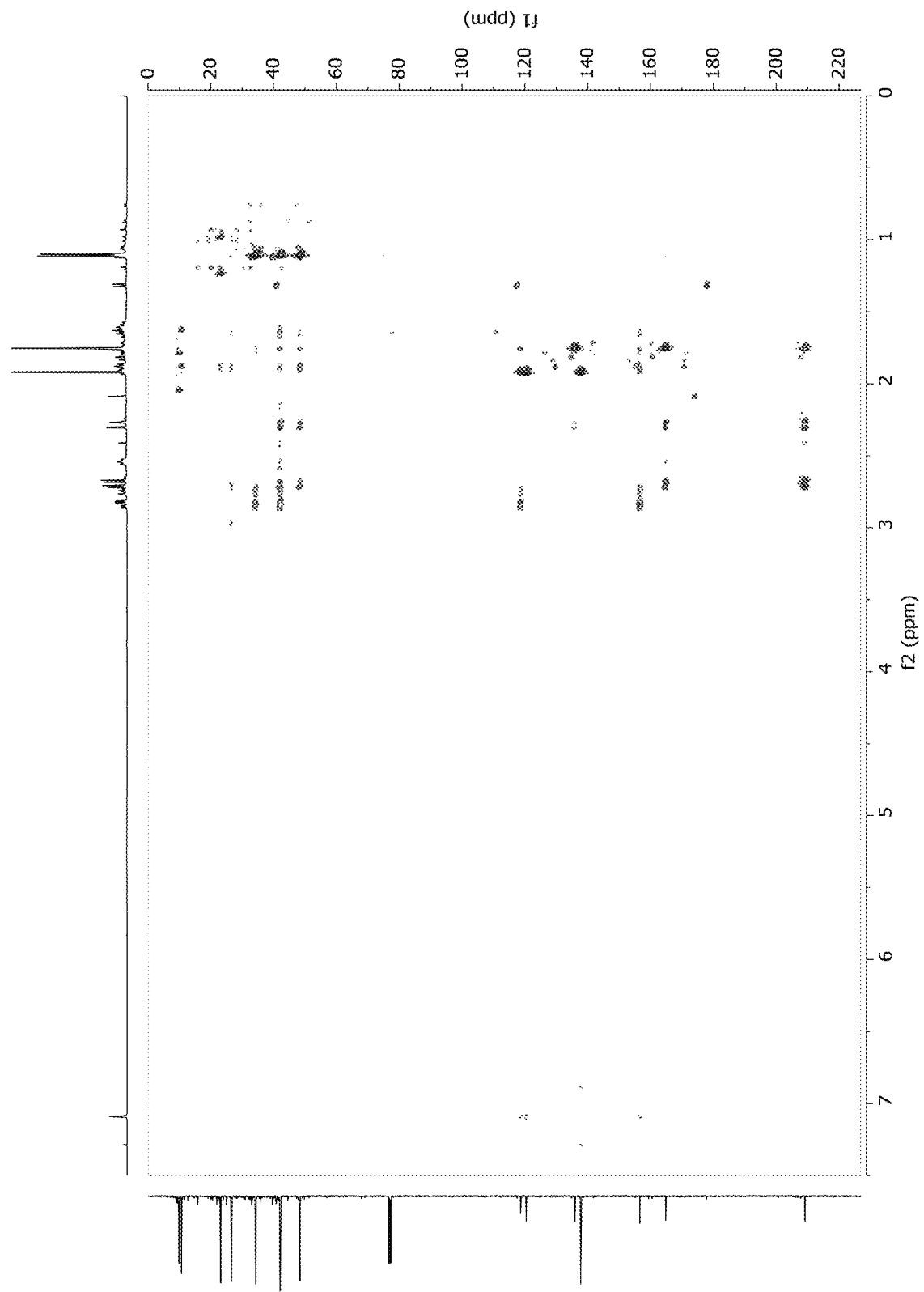
FIG. 5 shows the HMBC (500 MHz) spectrum of trans-Balaenone in CDCl$_3$.
Figure 6:
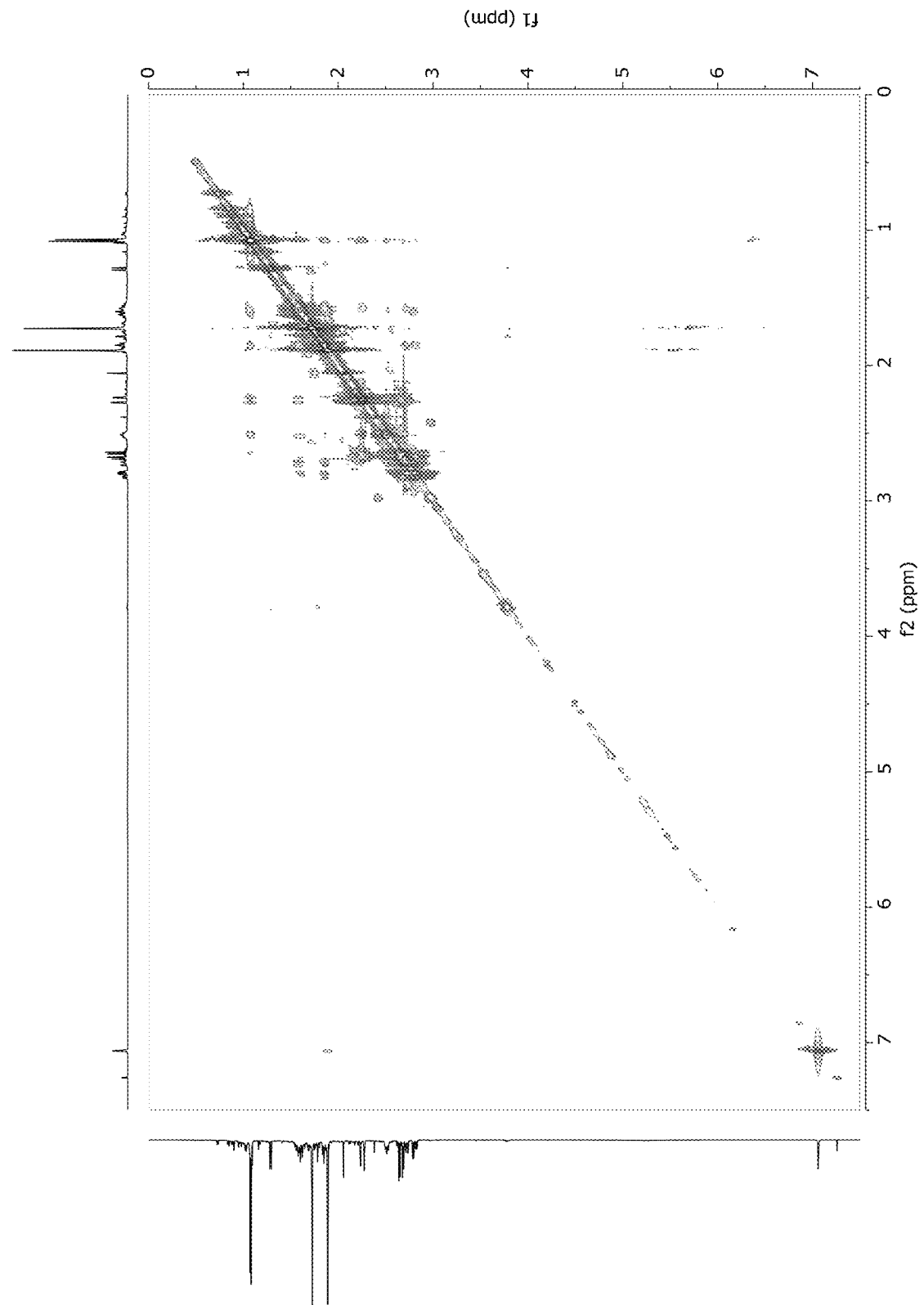
FIG. 6 shows the NOESY (500 MHz) spectrum of trans-Balaenone in CDCl$_3$.
Figure 8:
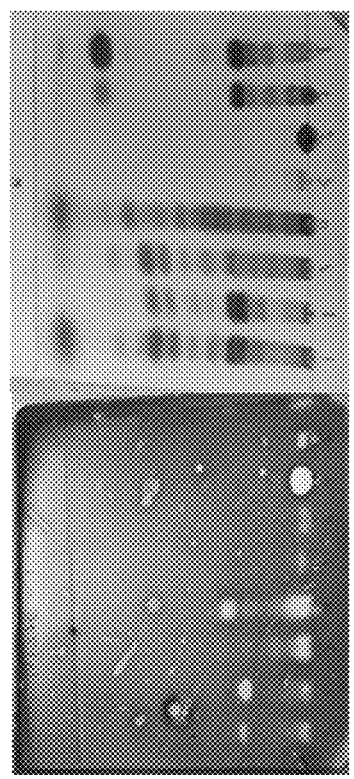

FIG. 8 shows the results of the antibacterial assay for *S. aureus* (left hand side) in comparison to the reference plate (right hand side). Sample 1=methanol extract, 2=60% acetone/water fraction, 3=80% acetone/water fraction, 4=100% acetone fraction. Bright pink/red spots in the reference plate are characteristic of Balaenone.

Figure 9:
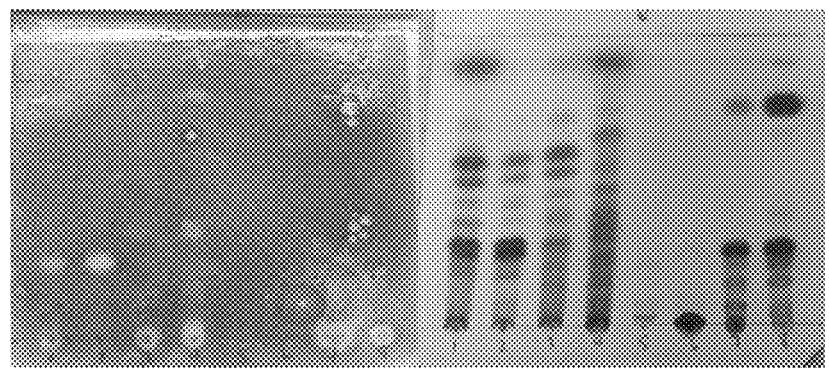

FIG. 9 shows the results of the antibacterial assay for *S. epidermidis* (left hand side) in comparison to the reference plate (right hand side). Sample 1=methanol extract, 2=60% acetone/water fraction, 3=80% acetone/water fraction, 4=100% acetone fraction. Bright pink/red spots in the reference plate are characteristic of Balaenone.

Figure 10:
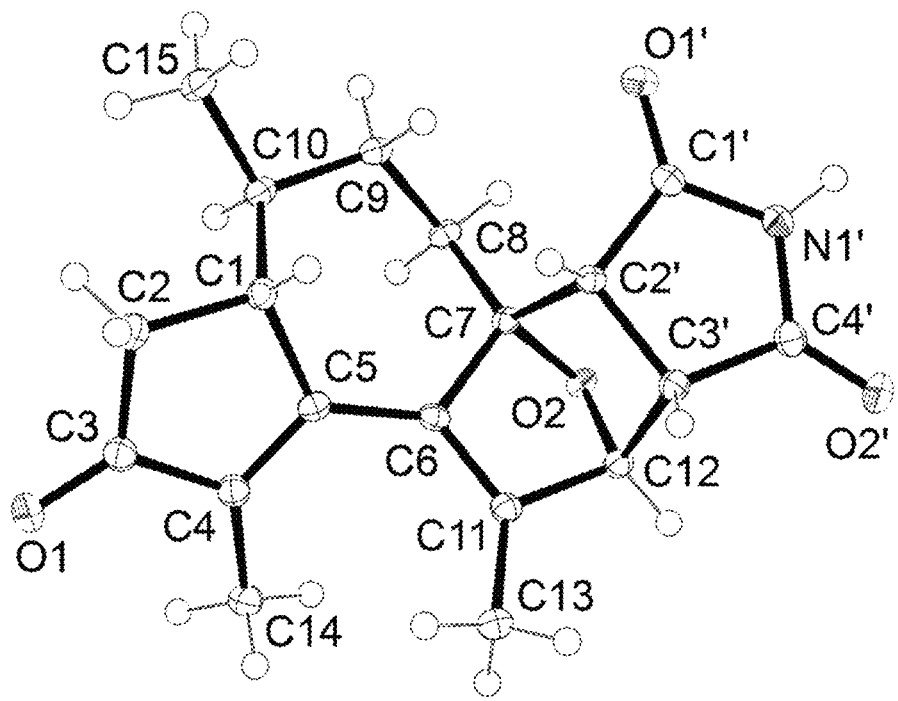

FIG. 10 is an ORTEP diagram of cycloaddition product (9).

Figure 11:
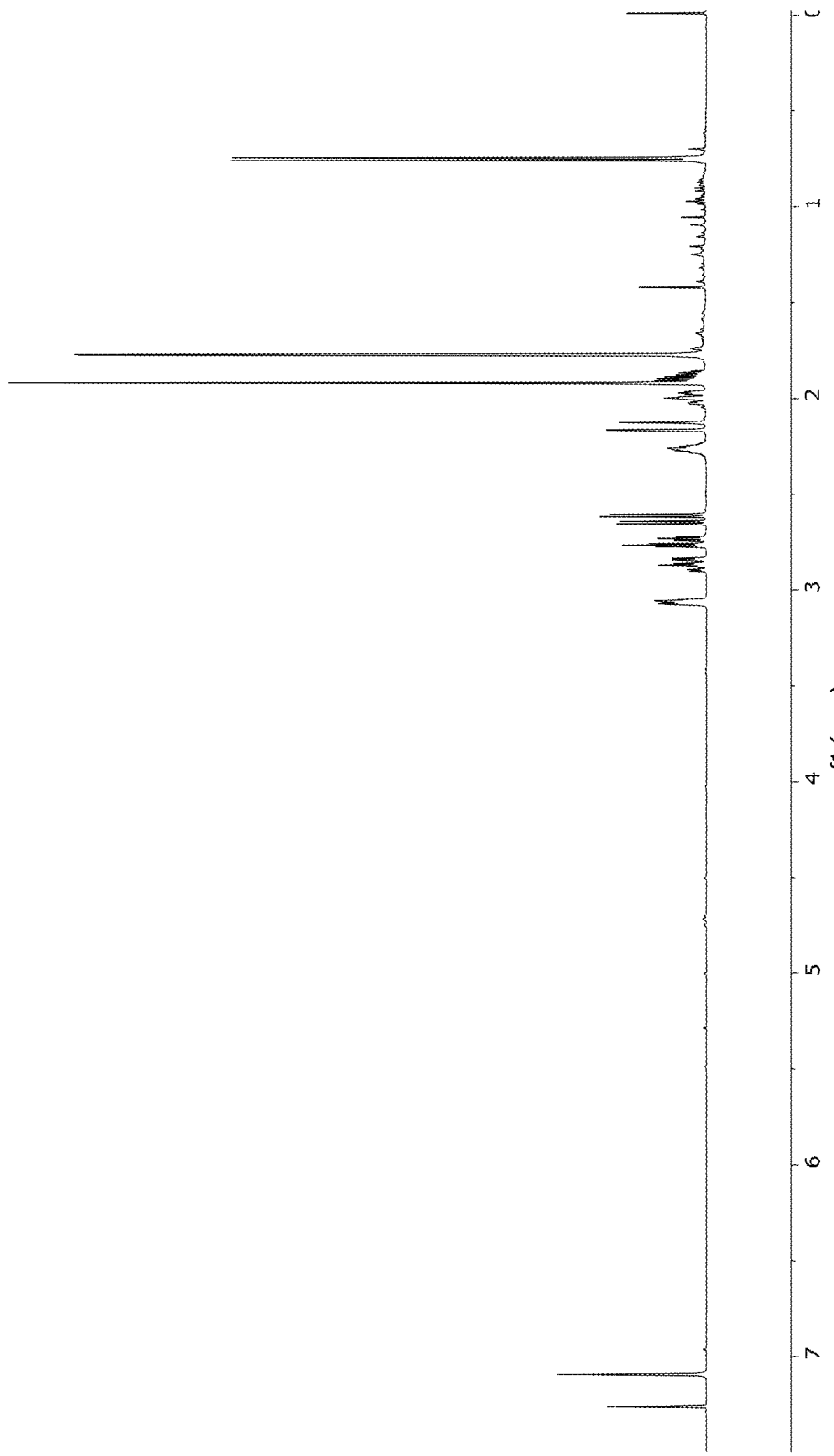

FIG. 11 shows the $^1$H NMR (500 MHz) spectrum of cis-Balaenone in CDCl$_3$.

Figure 12:
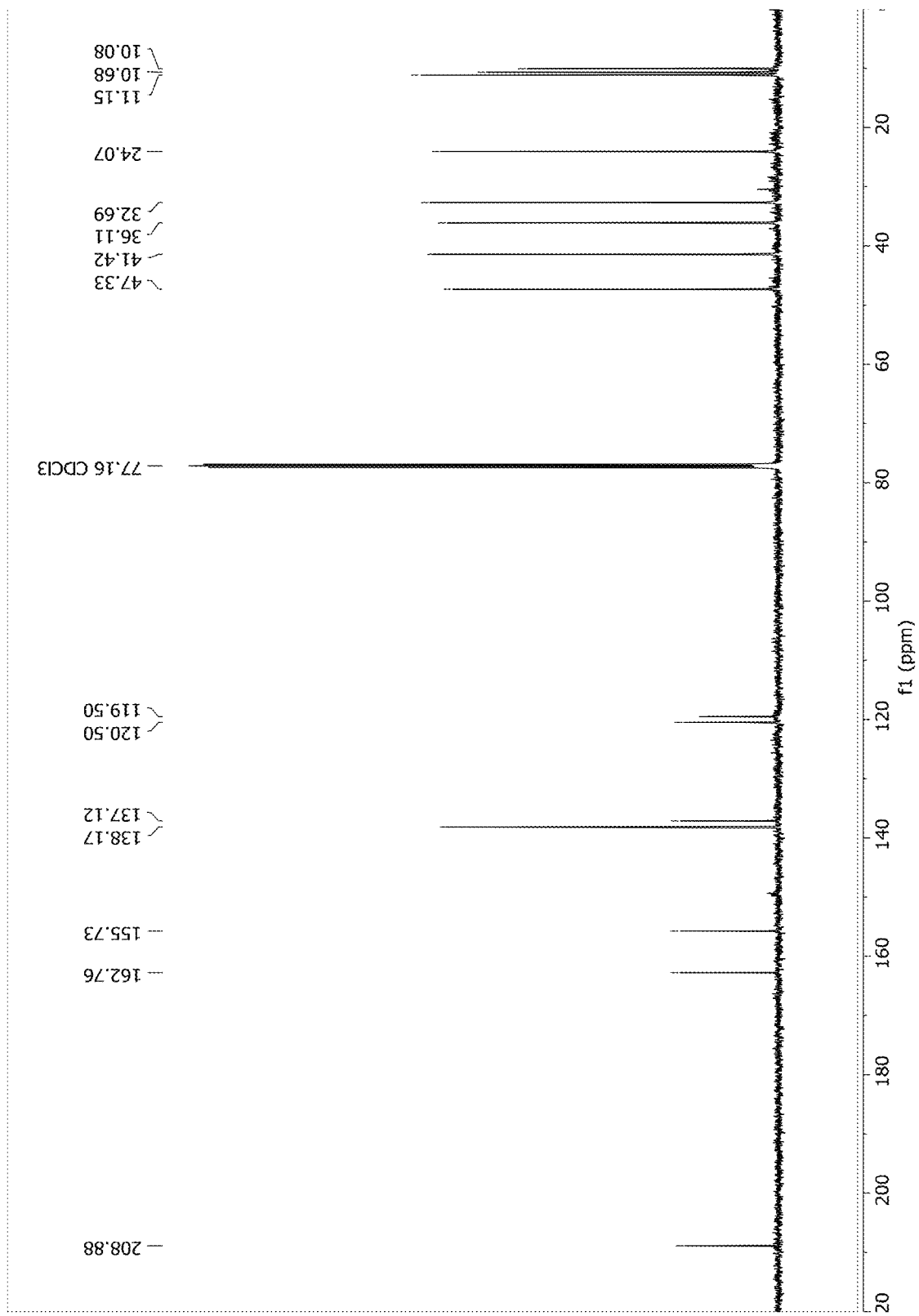

FIG. 12 shows the $^{13}$C NMR (125 MHz) spectrum of cis-Balaenone in CDCl$_3$.

Figure 13:
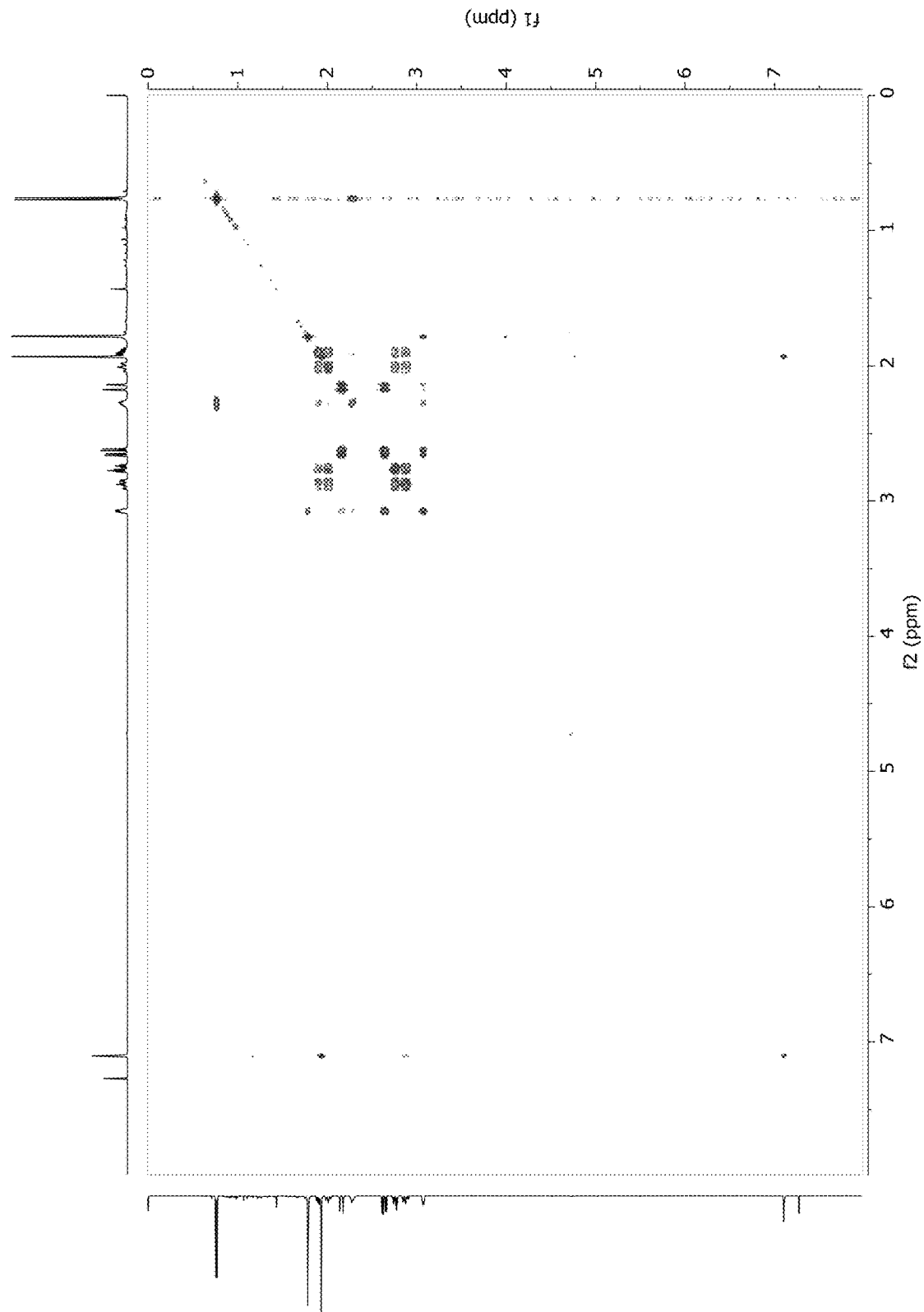

FIG. 13 shows the COSY (500 MHz) spectrum of cis-Balaenone in CDCl$_3$.

Figure 14:
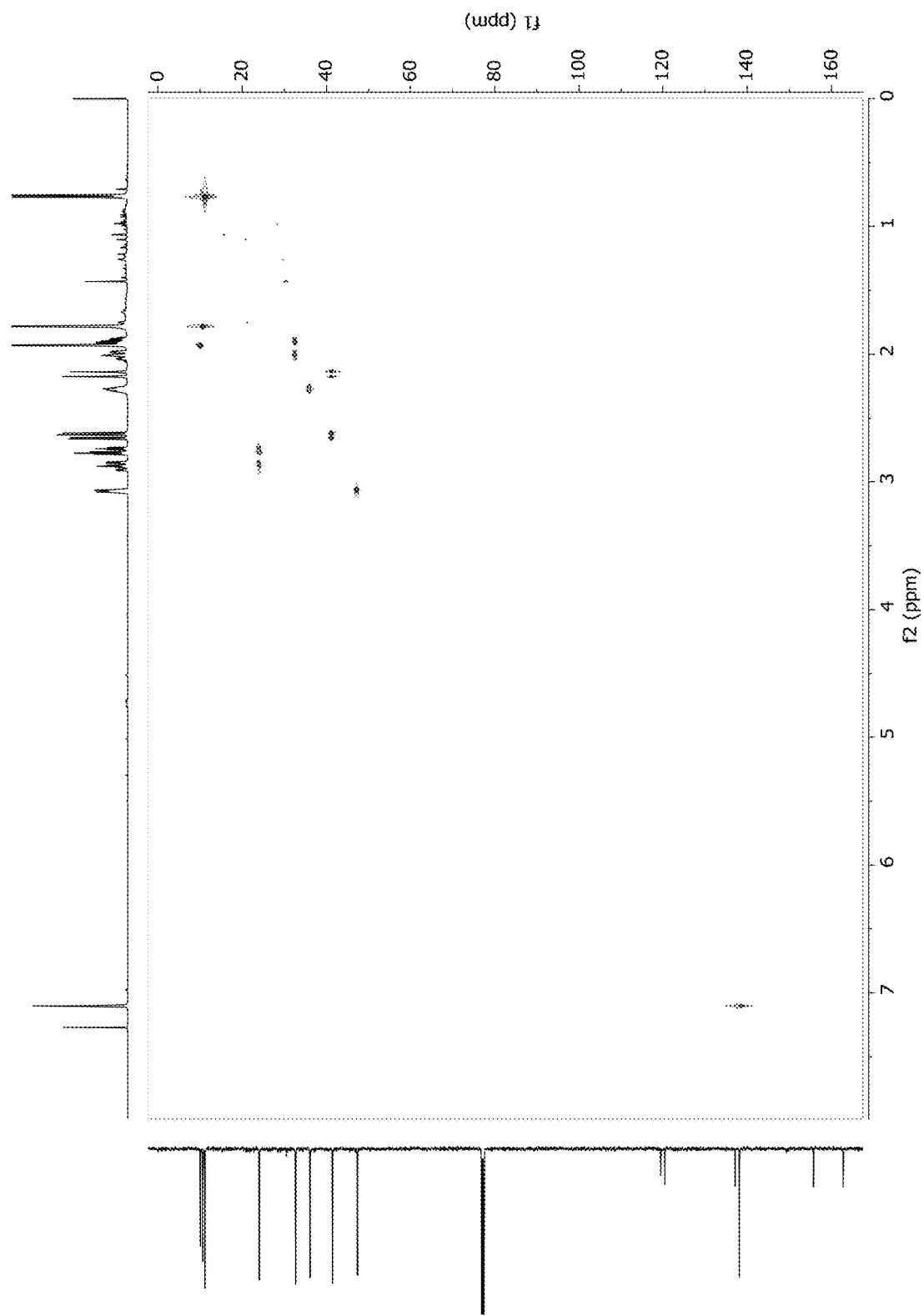

FIG. 14 shows the HSQC (500 MHz) spectrum of cis-Balaenone in CDCl$_3$.

Figure 15:
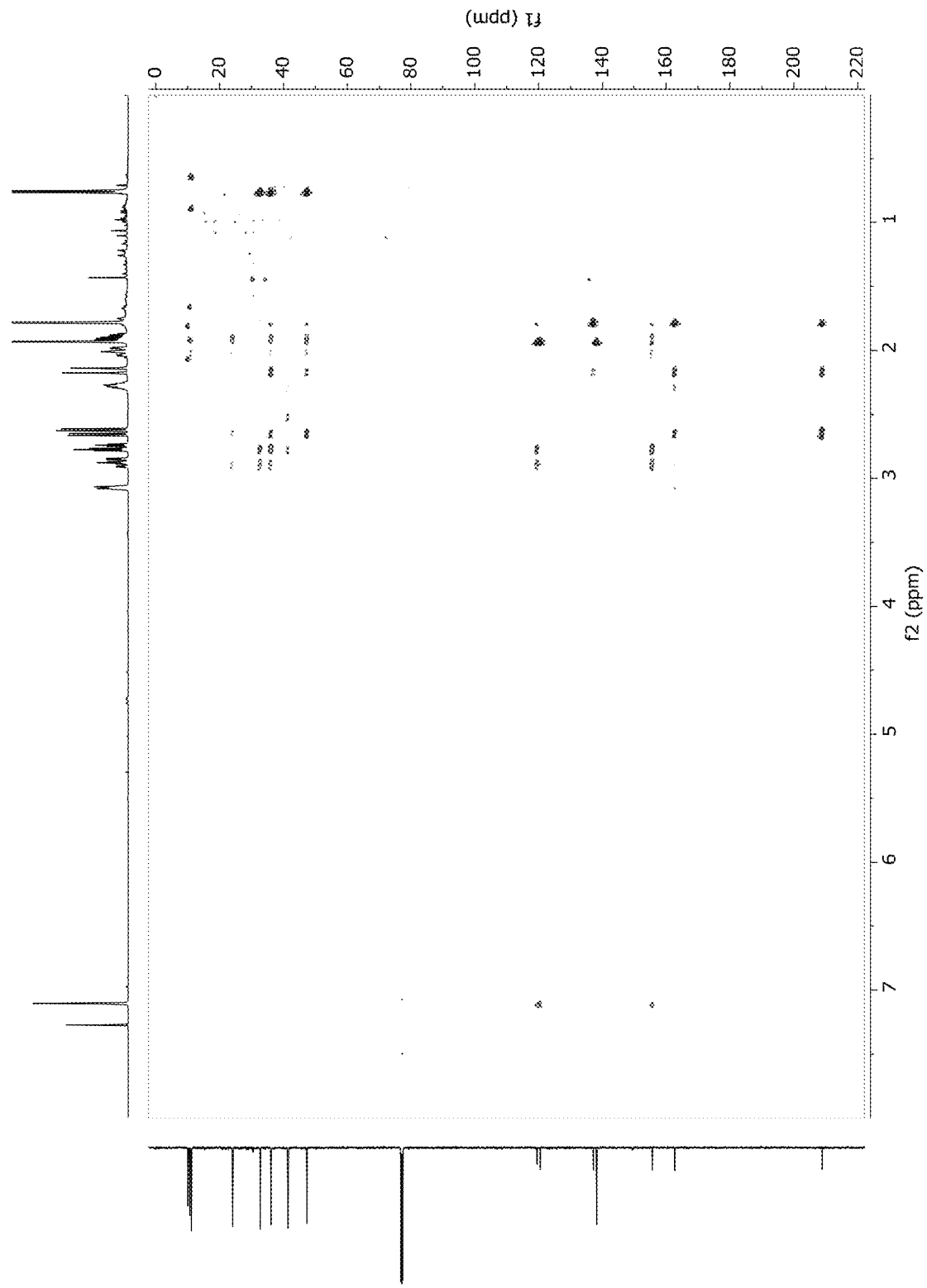

FIG. 15 shows the HMBC (500 MHz) spectrum of cis-Balaenone in CDCl$_3$.

Figure 16:
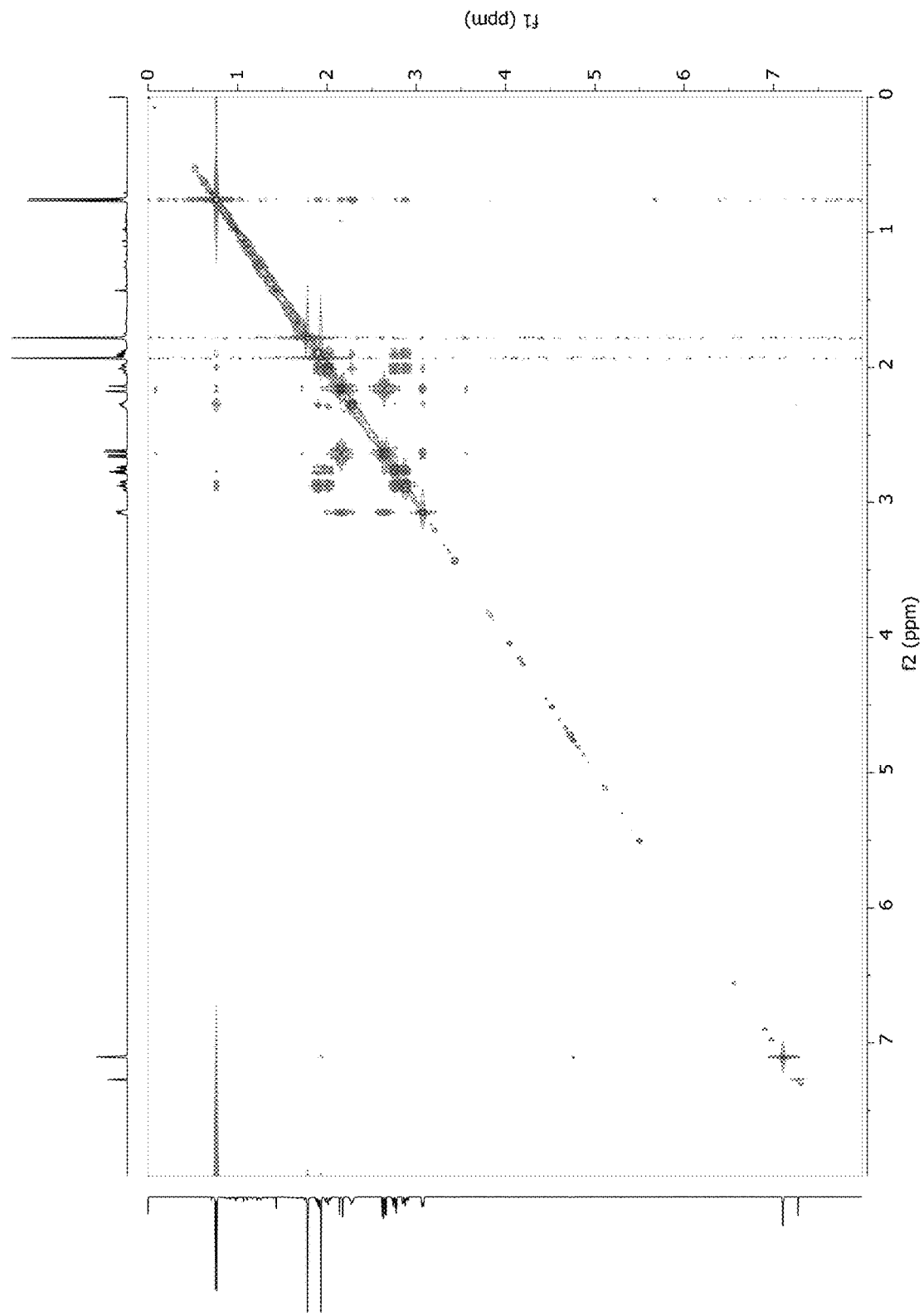

FIG. 16 shows the NOESY (500 MHz) spectrum of cis-Balaenone in CDCl$_3$.

5. DETAILED DESCRIPTION OF THE INVENTION

5.1 Definitions

The term "comprising" as used herein means "consisting at least in part of". When interpreting each statement in this specification and claims that includes the term "comprising", features other than that or those prefaced by the term may also be present. Related terms such as "comprise" and "comprises" are to be interpreted in the same manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

As used herein the term "and/or" means "and" or "or", or both.

The term "about" when used in connection with a referenced numeric indication means the referenced numeric indication plus or minus up to 10% of that referenced numeric indication. For example, "about 100" means from 90 to 110 and "about six" means from 5.4 to 6.6.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Asymmetric centres may exist in the compounds described herein. The asymmetric centres may be designated as (R) or (S), depending on the configuration of substituents in three-dimensional space at the chiral carbon atom. All chiral, diastereomeric and racemic forms of a structure are intended, unless a particular stereochemistry or isomeric form is indicated. All stereochemical isomeric forms of the compounds, including diastereomeric, enantiomeric, and epimeric forms, as well as d-isomers and l-isomers, and mixtures thereof, including enantiomerically enriched and diastereomerically enriched mixtures of stereochemical isomers, are within the scope of the invention unless otherwise indicated.

The compounds described herein may also exist as conformational or geometric isomers, including cis, trans, syn, anti, entgegen (E), and zusammen (Z) isomers. All such isomers and any mixtures thereof are within the scope of the invention unless otherwise indicated, Also within the scope of the invention are any tautomeric isomers or mixtures thereof of the compounds described. As would be appreciated by those skilled in the art, a wide variety of functional groups and other structures may exhibit tautomerism. Examples include, but are not limited to, keto/enol, imine/enamine, and thioketone/enethiol tautomerism.

Where the stereochemistry of a disclosed compound is named or depicted, the named or depicted stereoisomer can be at least 60%, 70%, 80%, 90%, 95%, 98%, 99% or 99.9% by weight pure relative to the all of the other stereoisomers. When a single enantiomer is named or depicted, the named or depicted enantiomer is at least 60%, 70%, 80%, 90%, 95%, 98%, 99% or 99.9% by weight pure relative to the other enantiomer.

The terms "administering" or "administration" as used herein refer to placement of the composition or compound of the invention into or onto a subject by a method appropriate to result in a therapeutic effect. The dosage form is selected and used as appropriate depending on the therapeutic purpose and the subject. The dose of the composition of the invention may be selected depending on the therapeutic purpose and the characteristics of the subject including their species, age, sex, general health and disease progression. In general, for human subjects, the compound of the invention may be administered in a dose of 0.01 to 100 mg, preferably 0.1 to 50 mg per day, per kg of body weight, either once or divided over several administrations.

A "therapeutically effective amount" as used herein is an amount sufficient to effect beneficial or desired results, including clinical results. A therapeutically effective amount can be administered in one or more administrations by various routes of administration. The therapeutically effective amount of the compound to be administered to a subject depends on, for example, the purpose for which the compound is administered, mode of administration, nature and dosage of any co-administered compounds, and characteristics of the subject, such as general health, other diseases, age, sex, genotype, body weight and tolerance to drugs. A person skilled in the art will be able to determine appropriate dosages having regard to these any other relevant factors.

A "subject" refers to a human or a non-human animal, preferably a vertebrate that is a mammal. Non-human mammals include, but are not limited to; livestock, such as, cattle, sheep, swine, deer, and goats; sport and companion animals, such as, dogs, cats, and horses; and research animals, such as mice, rats, rabbits, and guinea pigs. Preferably, the subject is a human.

5.2 Balaenone

The inventors have isolated a novel bioactive compound from an extract of the bark of the *M. latifolia* tree. The species of tree was identified by DNA fingerprint analysis which placed it amongst specimens of *M. latifolia* in the phylogenetic analysis of *Melicope* species conducted by Applelhans (Appelhans, Wen et al. 2014).

The novel compound of the invention is a furan-containing sesquiterpene with the structure shown in Formula (X). It is present in the bark of the *Melicope latifolia* tree in relatively high concentration. It can be obtained by methanolic extraction of bark, to provide a crude extract which can be purified using standard techniques in the art.

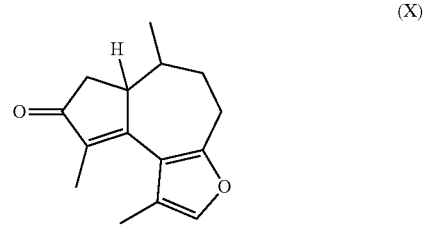 [SMILES: CC1=C2c3c(C)coc3CCC(C)C2CC1=O]

(X)

Balaenone possesses two stereogenic centres, making four stereoisomers possible (RR, RS, SR and SS). Extraction of Balaenone according to the method of the invention provides trans- and cis-Balaenone in an approximately 60:1 ratio. Each diastereoisomer is enantiomerically pure (>99%).

The absolute configuration of trans-Balaenone has been elucidated as described in Example 4. Based on the numbering system below, 1,10-trans-Balaenone is (+)-(1R,10S)-balaenone. Its IUPAC name is (6S,6aR)-1,6,9-trimethyl-5,6,6a,7-tetrahydroazuleno[5,4-b]furan-8(4H)-one.

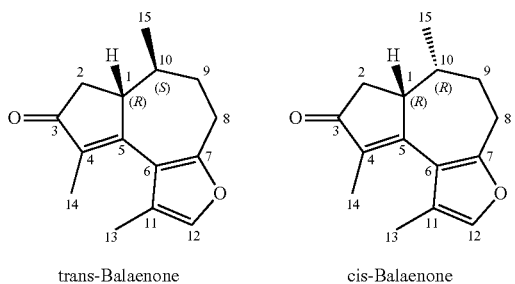

trans-Balaenone          cis-Balaenone

The absolute configuration of 1,10-cis-Balaenone has not been determined but its relative configuration is (+)-(1R*,10R*)-balaenone. Its IUPAC name is (6R*,6aR*)-1,6,9-trimethyl-5,6,6a,7-tetrahydroazuleno[5,4-b]furan-8(4H)-one.

The diastereomers can be separated from each other by flash chromatography, as described in Example 3.

Balaenone has not previously been reported and appears to represent a new class of compounds. In structure, Balaenone most closely resembles the melicophyllones A, B and C, as shown below.

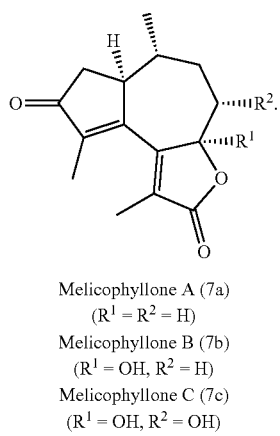

Melicophyllone A (7a)
($R^1 = R^2 = H$)
Melicophyllone B (7b)
($R^1 = OH, R^2 = H$)
Melicophyllone C (7c)
($R^1 = OH, R^2 = OH$)

These compounds were reported in 1988 and 1989 as components of the extracts of the root and stem bark of *Melicope triphylla* (Wu, Jong et al. 1988, Jong and Wu 1989). Balaenone may be the precursor to Melicophyllones A-C (7a-c) by way of oxidation of the furan to the (hydroxy) butenolide, with melicophyllone C (7c) in particular, differing by the additional oxidation of C-8. Although the relative stereochemistry of the melicophyllones was established, the absolute stereochemistry was not. Based on the elucidation of the absolute stereochemistry of trans-Balaenone described herein, it appears the stereochemistry selected by Wu and Jong (and shown above) to depict the melicophyllones was incorrect.

Balaenone has antibiotic properties and as such may be useful in the treatment of bacterial infections, particularly infections by Gram-positive bacteria.

Accordingly, in one aspect the invention provides bioactive Balaenone. In another aspect the invention provides a bioactive compound having the NMR spectrum of any one of FIGS. 1-6. In another aspect the invention provides a bioactive compound having the NMR spectrum of any one of FIGS. 11-16.

In one aspect the invention provides (+)-(6S,6aR)-1,6,9-trimethyl-5,6,6a,7-tetrahydroazuleno[5,4-b]furan-8(4H)-one.

In another aspect the invention provides the enantiomeric form of ((6R*,6aS*)-1,6,9-trimethyl-5,6,6a,7-tetrahydroazuleno[5,4-b]furan-8(4H)-one) that has a strong positive rotation.

5.3 Processes for Obtaining Balaenone and Purified Compositions of Balaenone

A variety of methods can be used to isolate and purify Balaenone from its source material utilising the standard techniques of natural product chemistry including solvent extraction, reversed phase chromatography, normal phase silica gel chromatography and the like.

Preferably, Balaenone and purified compositions of Balaenone are obtained from a methanol extract of the bark of the *M. latifolia* tree. Two useful approaches are the use of (a) reverse-phase chromatography with poly(styrene-divinylbenzene) co-polymer (PSDVB) and (b) liquid-liquid partitioning, optionally followed by normal phase chromatography, as described below. However, the person skilled in the art can use any combination of techniques that is effective.

Reverse-Phase Chromatography with PSDVB

In this extraction method, stem bark of *M. latifolia* is extracted with methanol (2x) for 18-24 hours. Both extracts are filtered and passed through a bed of PSDVB (second, followed by first extract) which has been pre-equilibrated in methanol. The eluents from this process are combined and diluted with an equal volume of water (50% methanol in water) and passed through the same PSDVB column. This process is repeated with another equivalent of water (to 25% methanol in water) and passed through the same PSDVB column. The column, now containing the adsorbed extract, is washed with water (3x column volume), followed by portions of i) 20% acetone in water (fraction A), ii) 40% acetone in water (fraction B), iii) 60% acetone in water (fraction C), iv) 80% acetone in water (fraction D), and v) acetone (fraction E).

Fractions C and D should contain quantities of Balaenone, with the former containing the majority of material.

Pure Balaenone can be obtained from Fraction C (60% acetone in water) by silica gel flash chromatography. A preferred solvent system is ethyl acetate in petroleum ether gradient (0-100%), where the Balaenone elutes from 20-25% ethyl acetate in petroleum ether.

Diastereomers of Balaenone can be separated by silica gel flash chromatography using 3:1 petroleum ether/diethyl ether, or an equivalent solvent system. The person skilled in the art would understand that other solvent systems could be used to purify Balaenone and its diastereomers.

Liquid-Liquid Partitioning

Stem bark of *M. latifolia* is extracted with methanol (2x) for 18-24 hours. Both extracts are combined, concentrated to dryness in vacuo, reconstituted in a water-immiscible organic solvent (e.g. dichloromethane) and partitioned with water. The organic layer is dried using anhydrous magnesium sulfate and concentrated to dryness in vacuo. The concentrated organic layer is purified by flash chromatography on silica gel using an ethyl acetate in petroleum ether gradient (0-100%), where Balaenone elutes from 20-25% ethyl acetate in petroleum ether.

Balaenone is easily tracked during the purification process using thin-layer chromatography (TLC) as it visualises as a bright pink/red spot when contacted with 5% v/v sulfuric acid in methanol+0.1% w/v vanillin in ethanol and heated.

It has an Rf of 0.25 when a sample on a silica gel TLC plate is run in 10% ethyl acetate in petroleum ether.

However, alternative visualisation systems can be used. Table 1 shows the Rf values of trans- and cis-Balaenone in a range of TLC solvent systems.

TABLE 1

| Solvent system | trans-Balaenone | cis-Balaenone |
| --- | --- | --- |
| 9:1 petroleum ether/ethyl acetate | 0.33 | 0.28 |
| dichloromethane | 0.13 | 0.13 |
| diethyl ether | 0.56 | 0.54 |
| 95:5 dichloromethane/acetone | 0.54 | 0.52 |
| 3:1 petroleum ether/diethyl ether | 0.23 | 0.19 |
| 95:5 dichloromethane/methanol | 0.83 | 0.81 |

Preferred extraction and isolated methods are described in the Examples section below.

In one aspect the invention provides a process of obtaining Balaenone or a purified composition of Balaenone, wherein the process comprises the steps of:
(a) extracting the bark of *M. latifolia* with methanol;
(b) passing the filtered methanol extract through a PSDVB column which has been pre-equilibrated in methanol;
(c) combining the eluent with an equal volume of water and passing it through the same PSDVB column;
(d) washing the column with water;
(e) eluting the compounds of the adsorbed extract with i) 20% acetone in water (fraction A), ii) 40% acetone in water (fraction B), iii) 60% acetone in water (fraction C), iv) 80% acetone in water (fraction D), and v) acetone (fraction E);
(f) collecting fractions C and/or D to provide a purified composition of Balaenone; and
(g) optionally, further purifying fractions C and/or D by silica gel flash chromatography to obtain a more purified composition of Balaenone.

In one embodiment, step (a) is repeated to provide a second methanolic extract.

In one embodiment, step (c) is repeated.

In one embodiment, fractions C and/or D are further purified in step (g) using an ethyl acetate in petroleum ether gradient (0-100%).

In one aspect the invention provides a process of obtaining trans-Balaenone and/or cis-Balaenone or a purified composition thereof, the process comprising the steps of:
(a) extracting the bark of *M. latifolia* with methanol;
(b) passing the filtered methanol extract through a PSDVB column which has been pre-equilibrated in methanol;
(c) combining the eluent with an equal volume of water and passing it through the same PSDVB column;
(d) washing the column with water;
(e) eluting the compounds of the adsorbed extract with i) 20% acetone in water (fraction A), ii) 40% acetone in water (fraction B), iii) 60% acetone in water (fraction C), iv) 80% acetone in water (fraction D), and v) acetone (fraction E);
(f) collecting fractions C and/or D to provide a purified composition of Balaenone;
(g) optionally, further purifying fractions C and/or D by silica gel flash chromatography using an ethyl acetate in petroleum ether gradient (0-100%) to obtain Balaenone, and
(h) separating trans- and cis-Balaenone on silica gel flash chromatography using an isocratic mixture of 3:1 petroleum ether/diethyl ether to obtain trans-Balaenone and cis-Balaenone.

In one aspect the invention provides a product obtained by the process of the above aspects.

In one embodiment the product is Balaenone or a purified composition of Balaenone. In one embodiment, the product is trans-Balaenone or a purified composition of trans-Balaenone. In one embodiment, the product is cis-Balaenone or a purified composition of cis-Balaenone.

5.4 Purified Compositions of Balaenone

In one aspect the invention provides a purified composition of Balaenone. In one embodiment, the invention provides a purified composition obtained by the process defined above.

As used herein, the term "purified" with reference to a composition of Balaenone, means that the composition comprises at least greater than 50% wt % Balaenone. Purity levels of 95, 96, 97, 98, 99 and even 100% are achievable using the methods outlined herein. Purity can be measured by HPLC.

In one embodiment, the purified composition comprises at least about 60, 65, 70, 75, 80, 85, 90, 95, 96, 97, 98 or 99 wt % Balaenone.

In one embodiment the purified composition comprises at least 60 wt % Balaenone.

In one embodiment the purified composition comprises at least 70 wt % Balaenone.

In one embodiment the purified composition comprises at least 80 wt % Balaenone.

In one embodiment the purified composition comprises at least 80 wt % Balaenone.

In one embodiment the purified composition comprises at least 90 wt % Balaenone.

In one embodiment the purified composition comprises at least 95 wt % Balaenone.

In one embodiment the purified composition comprises at least 98 wt % Balaenone.

In one embodiment the purified composition comprises at least 99 wt % Balaenone.

In one embodiment, the purified composition comprises at least about 60, 65, 70, 75, 80, 85, 90, 95, 96, 97, 98 or 99 wt % of trans-Balaenone. In one embodiment, the purified composition comprises at least about 60, 65, 70, 75, 80, 85, 90, 95, 96, 97, 98 or 99 wt % of cis-Balaenone.

In one embodiment the purified composition comprises less than about 2 wt % halifordin.

In one embodiment the purified composition comprises at least about 60, 65, 70, 75, 80, 85, 90, 95, 96, 97, 98 or 99 wt % Balaenone and less than 2% wt % halifordin.

In one embodiment the purified composition comprises at least about 60, 65, 70, 75, 80, 85, 90, 95, 96, 97, 98 or 99 wt % trans-Balaenone and less than 2% wt % halifordin.

In one embodiment the purified composition comprises at least about 60, 65, 70, 75, 80, 85, 90, 95, 96, 97, 98 or 99 wt % cis-Balaenone and less than 2% wt % halifordin.

In one embodiment, the purified composition consists essentially of at least about 60, 65, 70, 75, 80, 85, 90, 95, 96, 97, 98 or 99 wt % Balaenone. In one embodiment, the purified composition consists essentially of at least about 60, 65, 70, 75, 80, 85, 90, 95, 96, 97, 98 or 99 wt % of trans-Balaenone.

Pure trans-Balaenone was observed to be quite stable when stored at cool temperatures, away from light and oxygen. However, less pure compositions were found to degrade quickly at room temperature (within 2 days) to give melicophyllone B (7b). Final purification of trans-Balaenone on silica gel separated it from an oxygenated aromatic compound, subsequently identified as halifordin (8). Without being bound by theory, it is believed that degradation is due to the presence of halifordin (8), which is also present in the methanol extract of *M. latifolia*.

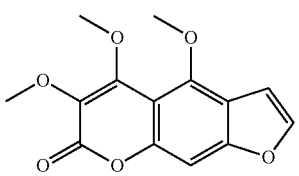

8

The conversion of trans-Balaenone to 7b is thought to occur in the presence of singlet oxygen. Halfordin (8) is structurally related to compounds (e.g. psoralen) known to be photoactivators of molecular oxygen to its reactive singlet state [$^1O_2$] (Aboul-Enein et al. 2003).

Singlet oxygen is known to react (Montagnon et al. 2014) with the furan moiety (such as is present in Balaenone) to form a butenolide moiety as in 7b (depicted with respect to trans-Balaenone in Scheme 1).

Scheme 1

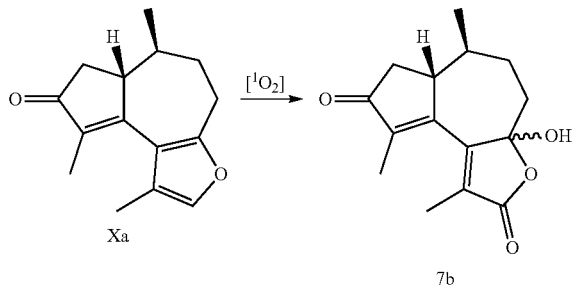

Xa

7b

It is believed that the same process would occur with respect to cis-Balaenone.

In the absence of 8, trans-Balaenone was essentially stable at room temperature when stored away from light and oxygen. In a separate experiment, purified trans-Balaenone was photochemically reacted with atmospheric oxygen in the presence of Rose Bengal (another known photogenerator of singlet oxygen), which generated 7b among other oxidation products.

Removal of halifordin (8) from the extract provides a purified composition of trans-Balaenone in which trans-Balaenone is stable at room temperature, when stored away from light and oxygen. It is believed that the same process would occur with respect to cis-Balaenone.

Accordingly, the purification process provides Balaenone or a purified composition of Balaenone that has markedly different properties to Balaenone as naturally found, ie in the bark of the *M. latifolia* tree.

In one embodiment the purified composition of Balaenone comprises less than about 2 wt % halifordin.

In one embodiment the purified composition comprises at least about 60, 65, 70, 75, 80, 85, 90, 95, 96, 97, 98 or 99 wt % Balaenone and less than 2% wt % halifordin.

In one embodiment the purified composition comprises at least about 60, 65, 70, 75, 80, 85, 90, 95, 96, 97, 98 or 99 wt % trans-Balaenone and less than 2% wt % halifordin. In one embodiment the purified composition comprises at least about 60, 65, 70, 75, 80, 85, 90, 95, 96, 97, 98 or 99 wt % cis-Balaenone and less than 2% wt % halifordin.

In one aspect the invention provides a purified composition consisting essentially of Balaenone. In one aspect the invention provides a purified composition consisting essentially of trans-Balaenone. In one aspect the invention provides a purified composition consisting essentially of cis-Balaenone.

In one embodiment, the purified composition of Balaenone, trans-Balaenone or cis-Balaenone comprises a solubilising agent. In one embodiment the solubilising agent is selected from cyclodextrin, alcohol, glycerine, propylene glycol and polyethylene glycol.

In one aspect the invention provides a pharmaceutical composition comprising Balaenone and one or more pharmaceutically acceptable excipients. In one aspect the invention provides a pharmaceutical composition comprising trans-Balaenone and one or more pharmaceutically acceptable excipients. In one aspect the invention provides a pharmaceutical composition comprising cis-Balaenone and one or more pharmaceutically acceptable excipients.

The term "pharmaceutical composition" as used herein, means a solid or liquid composition in a form, concentration and purity suitable for administration to an animal subject.

Balaenone may be formulated into a pharmaceutical composition by admixture with pharmaceutically acceptable excipients.

The term "pharmaceutically acceptable excipients" as used herein refers to substances which are physiologically inert, pharmacologically inactive and are compatible with the physical and chemical characteristics of the active agent. Pharmaceutically acceptable excipients include but are not limited to carriers, fillers, diluents, binders, disintegrants, plasticizers, viscosity agents, solvents, surfactants, preservatives, sweetening and flavouring agents, and pharmaceutical grade dyes and pigments.

Pharmaceutical compositions of Balaenone may be prepared for parenteral administration, particularly in the form of liquid solutions or suspensions in aqueous physiological buffer solutions; for oral administration, particularly in the form of tablets or capsules; for intranasal administration, particularly in the form of powders, drops or aerosols; and for topical administration, particularly in the form of emulsions or ointments. Compositions for other routes of administration may be prepared using standard methods known in the art, for example as described in Remington's Pharmaceutical Sciences 18$^{th}$ Ed., Gennaro, ed. (Mack Publishing Co. 1990).

In one embodiment the pharmaceutical composition is in the form of, or is formulated as a solid, liquid, paste, gel, emulsion, cream, ointment, lotion, liniment, solution, suspension, stick, block, pill, lozenge, powder or slurry.

5.5 Uses of Balaenone

As seen in Example 4, both pure Balaenone and purified compositions comprising Balaenone demonstrate antibacterial activity.

Accordingly, in one aspect the invention provides a method of treating a bacterial infection in a subject in need thereof, comprising administering to the subject a therapeutically effective amount of Balaenone or a purified composition of Balaenone.

In another aspect the invention relates to the use of Balaenone in the manufacture of a medicament for treating a bacterial infection and to a composition of Balaenone for use in treating a bacterial infection.

As Balaenone comprises a mixture of about 60:1 trans-Balaenone and cis-Balaenone, the biological activity ascribed to Balaenone is likely to derive from trans-Balaenone, although cis-Balaenone may also be active. Accordingly, in one embodiment the Balaenone is trans-Balaenone.

In one embodiment the infection is a Gram-positive bacterial infection.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

6. EXAMPLES

General Experimental Methods

Optical rotations were measured on a Rudolph Research Analytical Autopol IV polarimeter. UV/vis spectra were recorded on a Molecular Devices SpectraMax M3 spectrophotometer. NMR experiments were acquired on a Bruker 500 MHz spectrometer, operating at 500 MHz and 125 MHz for $^1$H and $^{13}$C nuclei, respectively. Accurate mass was determined using an Agilent 6530 Q-TOF mass spectrometer equipped with an Agilent 1260 HPLC system for solvent delivery utilising an electrospray ionization source in positive-ion mode. Flash chromatography was performed on a Büchi Reveleris X2 preparative chromatography system.

Solvents were of analytical grade quality or higher. Water was glass-distilled prior to use. Solvent mixtures are reported as % vol/vol, unless otherwise stated. Reversed-phase chromatography was performed with Supelco Diaion HP-20 poly(styrene-divinylbenzene) co-polymer (PSDVB). Silicycle SiliaFlash F60 silica gel (40-63 m) was used for dry loading. Pre-filled silica cartridges for flash chromatography were obtained from Silicycle. A stainless steel semi-preparative column (silica, 250×10 mm, 10 μm) was obtained from Büchi. TLC was conducted on 0.2 μm silica gel (60 F254) pre-coated plates, using 5% v/v sulfuric acid in methanol+0.1% w/v vanillin in ethanol, followed by heat to visualize.

Example 1: Isolation of Balaenone (100 g Plant Material Scale)

The fresh frozen stem bark of M. latifolia (100 g) was cut into small pieces (~2 cm$^3$) and soaked in 200 mL of methanol for 18 h. The methanol (first extract) was filtered and the bark material soaked in a further 200 mL of methanol for 18 h. This methanol (second extract) was filtered and passed through a 100 mL PSDVB (HP-20, Supelco) column with gravity and flow restricted to 2 mL/min.

The first extract was then passed through the same column in a similar manner and the eluents combined. 400 mL of H$_2$O was added to the eluent which was again passed through the PSDVB column at the same rate. The resulting eluent (800 mL) was diluted with a further 800 mL of water and passed through the same column. The column was then eluted with flow restricted to approx. 2 mL/min with 300 mL aliquots of: water (discarded), i) 20% acetone/water, ii) 40% acetone/water, iii) 60% acetone/water, iv) 80% acetone/water and v) acetone.

The 60% acetone/water fraction was diluted with 300 mL of water and passed through a 50 mL bed of PSDVB (HP-20). The eluent was further diluted with 600 ml of water, passed through the same PSDVB bed and the eluent discarded. The column was drained of liquid with a small amount of compressed air and eluted with 150 mL of acetone. The resulting eluent was evaporated to dryness.

Fraction iii) (60% acetone/water) was predominantly Balaenone and halifordin with minor amounts of related sesquiterpenes. Balaenone was purified on silica gel: 2 g of the 60% acetone fraction was dissolved in 3 mL of 1:1 methanol in dichloromethane and evaporated onto 4 g of silica gel. The loaded silica gel was placed into a dry-loading cartridge and placed upstream of a 40 g silica column. The column was eluted with petroleum ether and a gradient of 0-50% ethyl acetate/petroleum ether was applied over 15 column volumes. Minor related sesquiterpenoids were eluted first (0-5% ethyl acetate/petroleum ether) followed by pure Balaenone (10-30% ethyl acetate/petroleum ether) and finally halifordin (>30% ethyl acetate/petroleum ether).

Example 2: Isolation of Balaenone (600 g Plant Material Scale)

The stem bark of M. latifolia (600 g, fresh frozen) was extracted with methanol (2×1.2 L) overnight and filtered. The second and first extracts were passed through a 500 mL bed of PSDVB, pre-equilibrated in methanol. The combined eluents from this step were successively diluted with water (2× volume) and passed back through the same column until a final solution concentration of 25% methanol/water was achieved. The column was washed with water (1.5 L, collected with the loading eluent) and then eluted with 1.5 L portions of i) 20% acetone/water, ii) 40% acetone/water, iii) 60% acetone/water, iv) 80% acetone/water, and v) acetone.

A 2 g portion of the concentrated 60% acetone/water fraction (fraction iii) was purified using silica gel (40 g) flash chromatography [petroleum ether/ethyl acetate, 0-60% 16 column volumes (CV), 60-100% 3 CV, 100%, 2.9 CV, methanol 0.4 CV]. Balaenone eluted at 20-25% petroleum ether/ethyl acetate, alongside halifordin (35-40% petroleum ether/ethyl acetate).

Example 3: Isolation of trans- and cis-Balaenone

Fractions enriched with Balaenone obtained according to the process described in Example 1 were pooled and chromatographed on silica gel (10×150 mm, 10μ, flow rate 5 mL/min), using an isocratic mixture of 3:1 petroleum ether/diethyl ether. trans-Balaenone (compound of Formula (X$_a$)) eluted at 12.4 min, while cis-Balaenone (compound of Formula (X$_b$)) eluted at 15.2 min.

cis-Balaenone was isolated as a colourless, optically active solid ([a]$^{20}_D$+575). The molecular formula from accurate mass determination and constitutional structure elucidated by NMR experimental data (Table 2) are identical to that determined for trans-Balaenone. Although the absolute configuration of cis-Balaenone has not been determined, being a diastereomer of trans-Balaenone, it must have a syn relationship between H-1 and H-10.

Example 4: Structure Elucidation of trans-Balaenone trans-Balaenone is presented as an optically active colourless oil ([a]$^{20}_D$+171). The molecular formula of $C_{15}H_{18}O_2$ was obtained from high-resolution mass spectrometry (m/z 231.1383 [M+H]$^+$, calcd. 231.1380) which requires seven degrees of unsaturation. The $^{13}$C NMR spectrum of trans-Balaenone contains all 15 required resonances. Analysis of the $^{13}$C, DEPT and HSQC NMR experiments identified the 15 carbons to be further broken down into three methyls ($\delta_C$ 23.2, 10.7, 9.2), three methylenes ($\delta_C$ 42.0, 26.6, 34.3), three methines ($\partial_C$ 137.8, 48.4, 42.1) and six non-protonated carbons ($\delta_C$ 209.2, 164.8, 156.6, 135.9, 120.4, 118.7). All 18 hydrogens required by the proposed molecular formula are attached to carbon which indicates the absence of exchangeable protons. NMR data is summarised in Table 2.

COSY and HMBC experiments established three major substructures. The correlations used to establish the planar structure of trans-Balaenone are shown below, and detailed using the numbering shown in structure I.

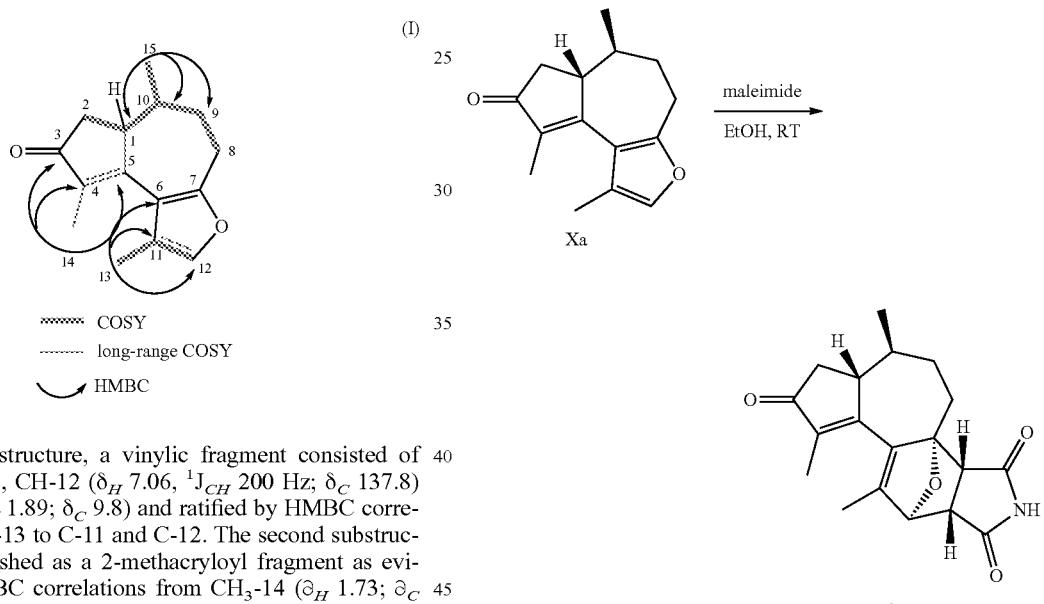

(I)

~~~~~~ COSY
------ long-range COSY
⌣ HMBC

The first substructure, a vinylic fragment consisted of C-11 ($\delta_C$ 120.4), CH-12 ($\delta_H$ 7.06, $^1J_{CH}$ 200 Hz; $\delta_C$ 137.8) and CH$_3$-13 ($\delta_H$ 1.89; $\delta_C$ 9.8) and ratified by HMBC correlations from H$_3$-13 to C-11 and C-12. The second substructure was established as a 2-methacryloyl fragment as evidenced by HMBC correlations from CH$_3$-14 ($\partial_H$ 1.73; $\partial_C$ 10.7) to C-3 ($\partial_C$ 209.2) C-4 ($\delta_C$ 135.9) and C-5 ($\delta_C$ 164.8). The third substructure, a 1,2,5-trisubstituted 3-methylpentyl unit consisting of CH$_2$-2 ($\partial_H$ 2.26, 2.67; $\delta_C$ 42.0), CH-1 ($\delta_H$ 2.52; $\partial_C$ 48.4), CH-10 ($\delta_H$ 1.58; $\delta_C$ 42.1), CH$_2$-9 ($\delta_H$ 1.60, 1.86; $\delta_C$ 34.3) and CH$_2$-8 ($\delta_H$ 2.73, 2.81; $\partial_C$ 26.6) The attachment of CH$_3$-15 ($\delta_H$ 1.08; $\delta_C$ 23.2) was established by a COSY correlation with H-10 and HMBC correlations to C-1, C-9 and C-10.

The relative configuration of trans-Balaenone was determined through analysis of scalar coupling constants and NOE correlation data. NOE correlations between H-1 with H-9a, and H-10 with H-8a both suggested a 1,3-pseudoaxial orientation about the seven-membered ring. These correlations place CH$_3$-15 pseudoequatorial to H-1 and H-9b and are supported in part by a vicinal coupling constant of 9.7 Hz between H-1 and H-10 indicating an anti-relationship of these two protons.

During the isolation process, a partially purified sample of trans-Balaenone underwent oxidation to another species. The planar structure of this compound was consistent with melicophyllone B (7b), a sesquiterpenoid first described by Wu et al. in 1988 from *M. triphylla*. The spectral details are identical, indicating the same relative configuration which was established by Wu et al. by single crystal X-ray diffraction analysis. The specific rotation of our experimentally-derived 7b ([α]$^{20}_D$ −199) is of the same sign as described in the literature {[α]$^{25}_D$ −38 (c 0.854, CHCl$_3$)}. From this it was concluded that trans-Balaenone and 7b share the same absolute configuration at their conserved stereogenic centres.

The absolute stereochemistry of trans-Balaenone was determined by X-ray crystallography of a trans-Balaenone derivative. trans-Balaenone (Formula X$_a$) was reacted with maleimide in a Diels-Alder cycloaddition experiment (in ethanol at room temperature). Four reaction products were detected—one of which (9) was isolated as a crystalline solid (Scheme 2). The X-ray structure of this adduct (FIG. 10) confirms the anti-relationship between H-1 and H-10 in the natural product (trans-Balaenone), and determines the absolute configuration as depicted (1R,10S).

Scheme 2

The relative stereochemistry of cis-Balaenone was elucidated by comparison to trans-balaenone.

Characterisation Data trans-Balaenone (X$_a$): colourless oil; [a]$^{20}_D$ +171 (c 0.5, CHC13); UV (MeOH) λ$_{max}$/nm (log ϵ) 244 (3.99), 280 (3.80); NMR (CDCl$_3$, 500 MHz) see Table 2; HRESIMS m/z 231.1383 [M+H]$^+$, calcd. for C$_{15}$H$_{19}$O$_2$, 231.1380.

Melicophyllone B (7b): colourless semi-crystalline solid; [a]$^{20}_D$ −199 (c 1, CHCl$_3$); NMR data as previously described by Wu et al.

Halfordin (3): colourless crystalline solid; HRESIMS m/z 277.0715 [M+H]$^+$ (calcd. for C$_{14}$H$_{13}$O6, 277.0707).

cis-Balaenone (X$_b$): colourless solid; [a]$^{20}_D$ +575 (c 1, CHCl$_3$); UV (MeOH) λ$_{max}$/nm (log ϵ) 226 (3.76), 256 (3.76), 298 (3.71); NMR (CDCl3, 500 MHz) see Table 3; HRESIMS m/z 231.1379 [M+H]+ (calcd. for C$_{15}$H$_{19}$O2, 231.1385).

TABLE 2

NMR Data (CDCl$_3$, 500 MHz) for trans-Balaenone (X$_a$)

| Position | $^{13}$C $\delta_C$ | mult. | $^1J_{CH}$ (Hz) | $^1$H $\delta_H$ | mult., J (Hz) | COSY | HMBC | NOESY |
|---|---|---|---|---|---|---|---|---|
| 1 | 48.4 | CH | | 2.52 | ddt, 9.7, 8.1, 1.7 | 2a, 2b, 10, 14 | 2, 3(w), 4(w), 5(w), 10 | 9a, 15 |
| 2 | 42.0 | CH$_2$ | | 2.26 | dd, 18.5, 1.7 | 1, 2b | 1, 3, 4, 5, 10 | 15 |
|   |      |         | | 2.67 | dd, 18.6, 6.3 | 1, 2a | 1, 3, 5, 10 | 15(w) |
| 3 | 209.2 | C | | | | | | |
| 4 | 135.9 | C | | | | | | |
| 5 | 164.8 | C | | | | | | |
| 6 | 118.7 | C | | | | | | |
| 7 | 156.6 | C | | | | | | |
| 8 | 26.6 | CH$_2$ | | 2.73 | ddd, 16.3, 11.0, 2.5 | 8b, 9a, 9b(w) | 6, 7, 9, 10 | 10 |
|   |      |        | | 2.81 | ddd, 16.2, 6.7, 2.0 | 8a, 9a(w), 9b | 6, 7, 9, 10 | 9a, 9b |
| 9 | 34.3 | CH$_2$ | | 1.60 | m | 8a, 8b(w), 9b | 1, 7, 8, 10, 15 | 1 |
|   |      |        | | 1.86 | m | 8a(w), 9a, 10 | | |
| 10 | 42.1 | CH | | 1.58 | m | 1, 9b, 15 | | 8a |
| 11 | 120.4 | C | | | | | | |
| 12 | 137.8 | CH | 200 | 7.06 | dq, 1.2, 0.6 | 13 | 6, 7, 11 | 13 |
| 13 | 9.8 | CH$_3$ | | 1.89 | d, 1.4 | 12 | 6, 11, 12, 7w | 12, 14 |
| 14 | 10.7 | CH$_3$ | | 1.73 | d, 1.6 | 1 | 3, 4, 5, 1w, 2w | 13 |
| 15 | 23.2 | CH$_3$ | | 1.08 | d, 6.3 | 10 | 1, 9, 10, 5w | 1, 2a, 2b(w), 9b |

TABLE 3

NMR Data (CDCl$_3$, 500 MHz) for cis-Balaenone (X$_b$).

| Position | $^{13}$C $\delta_C$ | mult. | $^1J_{CH}$ (Hz) | $^1$H $\delta_H$ | mult., J (Hz) | COSY | HMBC | NOESY |
|---|---|---|---|---|---|---|---|---|
| 1 | 47.3 | CH | | 3.06 | dsept (7.0, 1.6) | 2a, 2b, 10, 14 | 3, 5, 10, 15 | 9a(w), 9b, 10, 15 |
| 2 | 41.4 | CH$_2$ | | 2.15 | dd (18.5, 1.3) | 1, 2b | 1, 3, 4, 5, 10 | |
|   |      |        | | 2.64 | dd (18.4, 7.0) | 1, 2a | 1, 4, 5, 10 | |
| 3 | 208.9 | C | | | | | | |
| 4 | 137.1 | C | | | | | | |
| 5 | 162.8 | C | | | | | | |
| 6 | 119.5 | C | | | | | | |
| 7 | 155.7 | C | | | | | | |
| 8 | 24.1 | CH$_2$ | | 2.75 | dt (16.8, 4.3) | 8b, 9a, 9b | 6, 7, 9, 10 | |
|   |      |        | | 2.87 | ddd (16.7, 12.6, 4.0) | 8a, 9a, 9b, 12(w) | 6, 7, 9, 10 | 15 |
| 9 | 32.7 | CH$_2$ | | 1.90 | m | 8a, 8b, 9b, 10 | 1, 7, 8, 10 | 1(w) |
|   |      |        | | 2.00 | tdd (13.2, 3.9, 2.3) | 8a, 8b, 9a | 1(w), 7(w) | 1 |
| 10 | 36.1 | CH | | 2.27 | m | 1, 9a, 15 | | 1 |
| 11 | 120.5 | C | | | | | | |
| 12 | 138.2 | CH | 200* | 7.09 | quin (1.1) | 8b(w), 13 | 6, 7, 11 | 13 |
| 13 | 10.1 | CH$_3$ | | 1.92 | d (1.3) | 12 | 6, 11, 12 | 12 |
| 14 | 10.7 | CH$_3$ | | 1.78 | d (1.5) | 1 | 3, 4, 5, 6(w) | |
| 15 | 11.2 | CH$_3$ | | 0.75 | d (7.2) | 10 | 1, 9, 10 | 1, 2a, 2b(w), 8a, 8b, 9a |

*Obtained from HMBC leak-through.

Example 5: Antibacterial Activity of Balaenone and M. latifolia Bark Extracts The crude (1st methanolic) extract of M. latifolia bark and five chromatographic fractions obtained using the purification process outlined in Example 1 were submitted for TLC bioautography studies for qualitative determination of antibacterial activity.

Figure 7:
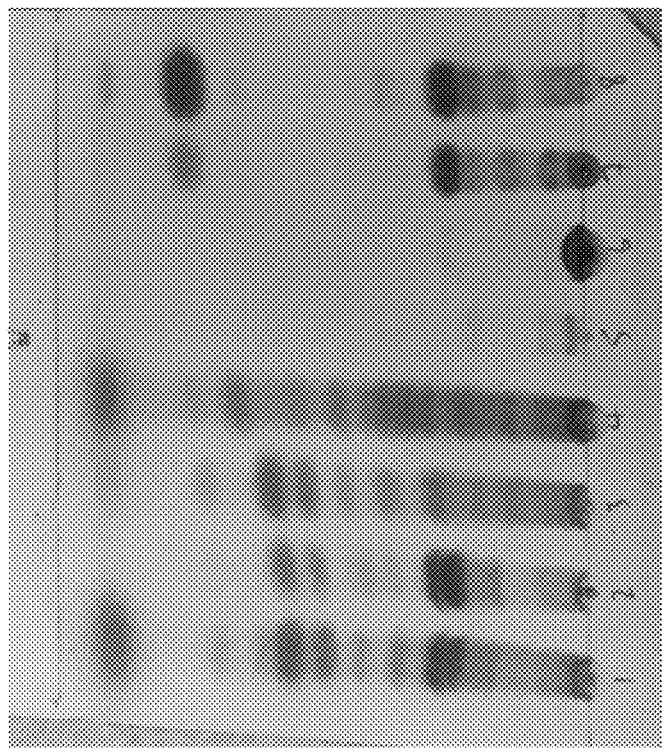
FIG. 7 shows a silica gel TLC plate displaying the separation and visualisation of the components of Sample 1=methanol extract, 2=60% acetone/water fraction, 3=80% acetone/water fraction, 4=100% acetone fraction. Bright pink/red spots are characteristic of Balaenone.

Briefly, a reference plate was prepared by loading the samples on a silica gel TLC plate which was developed using an established solvent system (10% ethyl acetate in petroleum ether) to separate their components based on polarity. The developed plates were then visualised using 5% v/v sulfuric acid in methanol+0.1% w/v vanillin in ethanol, followed by heat. Using this method, Balaenone was distinguished as a bright pink to red spot (see FIG. 7).

Multiple copies of this plate were then prepared and developed using the same solvent system, but instead are visualised by pouring agar inoculated/spiked with one of the following micro-organisms (see below) and allowed to incubate before visualisation with a reduction dye. Compounds present in these samples that display zones of inhibition are considered to possess antibacterial activity.

Gram-positive organisms tested (3):
Staphylococcus aureus, Staphylococcus epidermidis, Bacillus subtilis
Gram-negative organisms tested (2):
Pseudomonas aeruginosa, Escherichia coli The results with respect to S. aureus and S. epidermidis are shown in FIGS. 8 and 9. None of the extracts were found to be active against P. aeruginosa.

These results indicate that samples known to contain Balaenone exhibit antibacterial activity against S. aureus and *S. epidermidis*, with zones of inhibition appearing at the approximately same retention factor as the bright pink spot characteristic of Balaenone in the reference plate. No activity was observed against either Gram-negative organism.

Samples containing no Balaenone (20% and 40% acetone/water fractions) showed no activity against any of the selected organisms (not shown).

7. INDUSTRIAL APPLICATION

The compounds and compositions of the invention has application as antibiotics. Those persons skilled in the art will understand that the above description is provided by way of illustration only and that the invention is not limited thereto.

8. REFERENCES

Aboul-Enein H. Y., A. Kladna, I. Kruk, K. Lichszteld and T. Michalska (2003). "Effect of psoralens on Fenton-like reaction generating reactive oxygen species." Biopolymers 72: 59-68.

Appelhans, M. S., J. Wen and W. L. Wagner (2014). "A molecular phylogeny of *Acronychia, Euodia, Melicope* and relatives (Rutaceae) reveals polyphyletic genera and key innovations for species richness." Mol Phylogenet Evol 79: 54-68.

Bradacs, G., J. Hellmann and C. S. Weckerle (2011). "Medicinal plant use in Vanuatu: a comparative ethnobotanical study of three islands." Journal of Ethnopharmacology 137: 434-448.

Bradacs, G., L. Maes and J. Hellmann (2010). "In vitro cytotoxic, antiprotozoal and antimicrobial activities of medicinal plants from Vanuatu." Phytotherapy Research 24: 800-809.

Cambie, R. C., Y. J. Pan and B. F. Bowden (1996). "Flavonoids of the barks of *Melicope simplex* and *Melicope ternata*." Biochemical Systematics and Ecology 24: 461-462.

Chen, J. J., C. Y. Duh, H. Y. Huang and I. S. Chen (2003). "Furoquinoline alkaloids and cytotoxic constituents from the leaves of *Melicope semecarpifolia*." Planta Med 69: 542-546.

Chooi, O. H. (1994). "The ethnobotany of Citrus and their relatives." Korean Journal of Plant Taxonomy (Korea Republic) 24: 157-171.

Goh, S. H., V. C. Chung, C. K. Sha and T. C. W. Mak (1990). "Monoterpenoid phloroacetophenones from *Euodia latifolia*." Phytochemistry 29: 1704-1706.

Guo, N., L. Yu, R. Meng, J. Fan, D. Wang, G. Sun and X. Deng (2008). "Global gene expression profile of Saccharomyces cerevisiae induced by dictamnine." Yeast 25: 631-641.

Hashim, N. M. (2010). "Chemical Constituents and Biological Activity of Four *Melicope* Species (Rutaceace)." MSc, Universiti Putra Malaysia.

Jong, T. T. and Wu, T. S. (1989) "Chemical and biological investigation of *Melicope triphylla*. "The structures of three novel skeletal sesquiterpene lactones: melicophyllone A, B and C." J. Chem. Res., M: 1701-1709.

Montagnon T., D. Kalaitzakis, M. Triantafyllakis, M. Stratakis and G. Vassilikogiannakis (2014). "Furans and singlet oxygen—why there is more to come from this powerful partnership." Chem. Commun. 50: 15480-15498.

Primastuti, H. D. (2017). Isolation of Benzopyran Compounds from Fruit of *Melicope latifolia* and Antifeedant Test Towards Cabbage (ISOLASI SENYAWA BENZOPIRAN DARI BUAH *Melicope latifolia* DAN UJI ANTIFEEDANT TERHADAP ULAT KUBIS), Universitas Airlangga, Indonesia.

Wahyuni, T. S., L. Tumewu, A. A. Permanasari, E. Apriani, M. Adianti, A. Rahman, A. Widyawaruyanti, M. I. Lusida, A. Fuad, Soetjipto, Nasronudin, H. Fuchino, N. Kawahara, I. Shoji, L. Deng, C. Aoiki and H Hotta (2013) "Antiviral activities of Indonesian medicinal plants in the East Java region against hepatitis C virus" Virology Journal 10:259.

Wu, T.-S., T.-T. Jong, W.-M. Ju, A. T. McPhail, D. R. McPhail and K.-H. Lee (1988). "Structures and stereochemistry of melicophyllone A and hypocholesterolemic melicophyllone B, novel sesquiterpene lactones from *Melicope triphylla*." J. Chem. Soc., Chem. Commun. (14), 956-957.

We claim:
1. A pharmaceutical composition, comprising a bioactive compound of Formula (X):

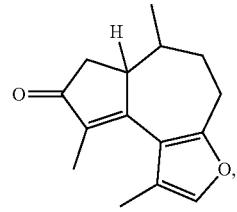

(X)

wherein the composition does not contain halifordin.

2. The composition of claim 1, comprising a bioactive compound of Formula (Xa):

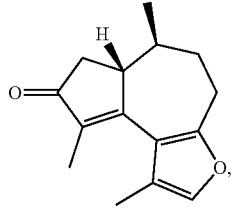

(Xa)

wherein a proportion of the compound of Formula (Xa) in the composition is at least 99% by weight based on a total weight of the composition.

3. The composition of claim 1, comprising a bioactive compound of Formula (Xb):

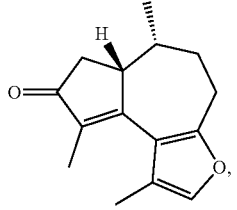

(Xb)

wherein a proportion of the compound of Formula (Xb) in the composition is greater than 99% by weight based on a total weight of the composition.

4. A composition, comprising at least 60 wt % of an isolated bioactive compound of Formula (X):

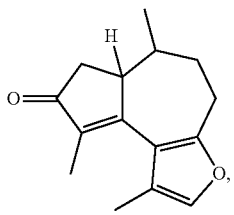
(X)

wherein the composition comprises less than about 2 wt % of halifordin.

5. The composition of claim 4, comprising at least 90 wt % of the compound of claim 1.

6. The composition of claim 5, comprising at least 95 wt % of the compound.

7. The composition of claim 4, further comprising one or more pharmaceutically acceptable excipients.

8. The composition of claim 4, further comprising a solubilizing agent.

9. The composition of claim 8, wherein the solubilizing agent is selected from the group consisting of cyclodextrin, alcohol, glycerine, propylene glycol and polyethylene glycol.

10. The composition of claim 7, further comprising a solubilizing agent.

11. The composition of claim 10, wherein the solubilizing agent is selected from the group consisting of cyclodextrin, alcohol, glycerine, propylene glycol and polyethylene glycol.

12. A method for obtaining a compound of Formula (X):

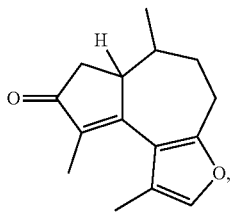
(X)

the method comprising:
(a) extracting bark of *M. latifolia* with methanol to obtain an extract, and filtering the extract to obtain a filtered extract;
(b) passing the filtered extract through a PSDVB column which has been pre-equilibrated in methanol, to obtain an eluent;
(c) combining the eluent with an equal volume of water to obtain a combination of eluent and water, and passing the combination through the PSDVB column used in (b);
(d) washing the PSDVB column with water;
(e) eluting adsorbed compounds of the filtered extract from the PSDVB column by (e) sequentially passing through the column:
   i) 20% acetone in water (fraction A),
   ii) 40% acetone in water (fraction B),
   iii) 60% acetone in water (fraction C),
   iv) 80% acetone in water (fraction D), and
   v) acetone (fraction E);
(f) collecting fractions C and/or D to provide a purified composition comprising the compound; and
optionally, further purifying fractions C and/or D by silica gel flash chromatography to obtain the compound.

13. A method of treating a bacterial infection in a subject in need thereof, the method comprising administering to the subject a therapeutically effective amount of an isolated bioactive compound of Formula (X):

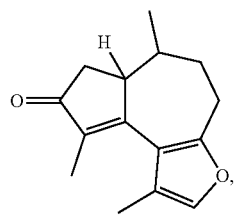
(X)

wherein the bacterial infection is a Staphylococcus bacterial infection.

14. The method of claim 13, wherein the Staphylococcus bacterial infection is *Staphylococcus aureus* or *Staphylococcus epidermidis*.

* * * * *